(12) United States Patent
White et al.

(10) Patent No.: US 11,141,709 B2
(45) Date of Patent: Oct. 12, 2021

(54) AUTOMATED EXPOSITION OF KNOWN AND NOVEL MULTIPLE MYELOMA GENOMIC VARIANTS USING A SINGLE SEQUENCING PLATFORM

(71) Applicants: Washington University, Saint Louis, MO (US); Multiple Myeloma Research Foundation, Norwalk, CT (US)

(72) Inventors: Brian White, Seattle, WA (US); Irena Lanc, St. Louis, MO (US); Robert Fulton, Worden, IL (US); Daniel Auclair, Middletown, CT (US); Michael H. Tomasson, Coralville, IA (US)

(73) Assignee: Washington University, St. Louis, MO (US)

( * ) Notice: Subject to any disclaimer, the term of this patent is extended or adjusted under 35 U.S.C. 154(b) by 770 days.

(21) Appl. No.: 15/804,924

(22) Filed: Nov. 6, 2017

(65) Prior Publication Data

US 2018/0126354 A1    May 10, 2018

Related U.S. Application Data

(60) Provisional application No. 62/418,049, filed on Nov. 4, 2016.

(51) Int. Cl.
*B01J 19/00*     (2006.01)
*C40B 40/06*    (2006.01)
(Continued)

(52) U.S. Cl.
CPC .......... *B01J 19/0046* (2013.01); *C12P 19/34* (2013.01); *C12Q 1/686* (2013.01); *C12Q 1/6827* (2013.01);
(Continued)

(58) Field of Classification Search
CPC .... C12Q 1/6827; C12Q 1/686; C12Q 1/6886; C12Q 2600/156; C40B 40/06;
(Continued)

(56) References Cited

U.S. PATENT DOCUMENTS

2013/0005613 A1    1/2013    Leamon et al.
2014/0256571 A1    9/2014    Konvicka

OTHER PUBLICATIONS

Bolli (Nature Communications, 2014, 5:2997) (Year: 2014).*
(Continued)

*Primary Examiner* — Jeremy C Flinders
(74) *Attorney, Agent, or Firm* — Stinson LLP

(57) ABSTRACT

A sequencing capture array for identifying mutations in Multiple Myeloma is disclosed. Also disclosed are targeted next generation sequencing methods for identifying SNV, CNV, and translocation mutations in Multiple Myeloma tumor cells. A capture array representing fewer than 500 genes implicated in Multiple Myeloma can be used to analyze tumor mutations and create a personalized treatment plan for a Multiple Myeloma patient. Analytical methods are presented that allow tumor mutations to be elucidated with coverage at a sequencing depth of no more than 500×, or as low as 100×, with optimal efficiency achieved at a sequencing depth of about 300×.

7 Claims, 10 Drawing Sheets
(8 of 10 Drawing Sheet(s) Filed in Color)
Specification includes a Sequence Listing.

(51) Int. Cl.
*C12Q 1/686* (2018.01)
*C12P 19/34* (2006.01)
*C12Q 1/6886* (2018.01)
*C12Q 1/6827* (2018.01)
*G16B 20/10* (2019.01)
*G16B 30/10* (2019.01)
*G16B 20/40* (2019.01)
*G16B 20/20* (2019.01)
*G16B 30/00* (2019.01)
*G16B 20/00* (2019.01)

(52) U.S. Cl.
CPC .......... *C12Q 1/6886* (2013.01); *C40B 40/06* (2013.01); *G16B 20/10* (2019.02); *G16B 20/20* (2019.02); *G16B 20/40* (2019.02); *G16B 30/10* (2019.02); *B01J 2219/00387* (2013.01); *B01J 2219/00722* (2013.01); *C12Q 2600/156* (2013.01); *G16B 20/00* (2019.02); *G16B 30/00* (2019.02)

(58) Field of Classification Search
CPC .................. C12P 19/03; B01J 19/0046; B01J 2219/00387; B01J 2219/00722
See application file for complete search history.

(56) References Cited

OTHER PUBLICATIONS

Bolli, N., et al. A DNA target-enrichment approach to detect mutations, copy number changes and immunoglobulin translocations in multiple myeloma., Blood Cancer J., 2016, 6, e467.

Chapman, M.A., et al., Initial genome sequencing and analysis of multiple myeloma., Nature, 2011, 471, 467-472.

Cottrell, C.E., et al. Validation of a next-generation sequencing assay for clinical molecular oncology., J. Mol. Diagn., 2014, 16, 89-105.

Futreal, P. A., et al. A census of human cancer genes., Nat. Rev. Cancer., 2004, 4, 177-183.

Frampton, G.M., et al., Development and validation of a clinical cancer genomic profiling test based on massively parallel DNA sequencing., Nat Biotechnol, 2013, 31, 1023-1031.

Garofalo, A, et al., The impact of tumor profiling approaches and genomic data slialegies for cancer precision medicine., Genome Med, 2016, 8, 79.

Kasar, S., et al. Whole-genome sequencing reveals activation-induced cytidine deaminase signatures during indolent chronic lymphocytic leukaemia evolution. Nat Commun, 2015, 6, 8866.

Kourtum, K.M., et al., Targeted sequencing using a 47 gene multiple myeloma mutation panel (M(3) P) in-17p high risk disease, Br. J. Haematol., 2015 168, 507-510.

Kortuem, K.M., et al., Longitudinal analysis of 25 sequential sample-pairs using a custom multiple myeloma mutation sequencing panel (M(3)P)., Ann. Hematol., 2015, 94, 1205-1211.

Kortuem, K.M., et al., Panel sequencing for clinically oriented variant screening and copy number detection in 142 untreated multiple myeloma patients., Blood Cancer J., 2016, 6, e397.

Kuiper, R., et al., Prediction of high- and low-risk multiple myeloma based on gene expression and the International Staging System., Blood, 2015, 126,1996-2004.

Manier S, et al., Genomic complexity of multiple myeloma and its clinical implications, Nat Rev Clin Oncol., 2017, 14,100-113 (Published online Aug. 2016).

Martinez-Lopez, J, et al., Prognostic value of deep sequencing method for minimal residual disease detection in multiple myeloma, Blood, 2014, 123, 3073-3079.

Morgan, G.J., et al., The genetic architecture of multiple myeloma. Nat Rev Cancer, 2012, 12, 335-348.

Kortuem, K. M., et al., Development and Results of a Multiple Myeloma Specific Custom 77-Gene Mutation Panel for Clinical Targeted Sequencing., Blood, 2014, 124, 169.

Adzhubei, I.A., et al. A method and server for predicting damaging missense mutations. Nat Methods, 2010, 7, 248-249.

Bolli, N., et al., Heterogeneity of genomic evolution and mutational profiles in multiple myeloma., Nat Commun, 2014, 5, 2997.

Cheng DT, et al. Memorial Sloan Kettering Integrated Mutation Profiling of Actionable Cancer Targets (MSK-IMPACT): A Hybridization Capture Based Next-Generation Sequencing Clinical Assay for Solid Tumor Molecular Oncology., J. Mol. Diagn., 2015, 17, 251-264.

* cited by examiner

```
                            SEQUENCE LISTING

<160> NUMBER OF SEQ ID NOS: 11

<210> SEQ ID NO 1
    <211> LENGTH: 315
    <212> TYPE: DNA
    <213> ORGANISM: Homo sapiens

<400> SEQUENCE: 1 tttttaatt aattgagcga agctggaagc agatgatgaa ttagagtcaa gatggctgca       60
tgggggtctc cggcacccac agcaggtggc aggaagcagg tcaccgcgag agtctatttt     120
aggaagcaaa aaaacacaat tggtaaattt atcacttctg gttgtgaaga ggtggttttg     180
cccagcccag atctgaaagt gctctactga gcaaaacaac acctggacaa tttgcgtttc     240
taaaataagg cgaggctgac cgaaactgaa aaggcttttt ttaactatct gaatttcatt     300
tccaatctta gctta                                                      315

<210> SEQ ID NO 2
    <211> LENGTH: 20
    <212> TYPE: DNA
    <213> ORGANISM: Homo sapiens

<400> SEQUENCE: 2
accactaaca ggggacatgc                                                  20

<210> SEQ ID NO 3
    <211> LENGTH: 20
    <212> TYPE: DNA
    <213> ORGANISM: Homo sapiens

<400> SEQUENCE: 3
tttgattatt cccccaacca                                                  20

<210> SEQ ID NO 4
    <211> LENGTH: 20
    <212> TYPE: DNA
    <213> ORGANISM: Homo sapiens

<400> SEQUENCE: 4
acaagccaga ggagtgagga                                                  20

<210> SEQ ID NO 5
    <211> LENGTH: 20
    <212> TYPE: DNA
    <213> ORGANISM: Homo sapiens

<400> SEQUENCE: 5
```

-continued

```
ctctgaagac caggctcacc                                               20

<210> SEQ ID NO 6
<211> LENGTH: 20
<212> TYPE: DNA
<213> ORGANISM: Homo sapiens

<400> SEQUENCE: 6
gggctgtgtc tctgtggtat                                               20

<210> SEQ ID NO 7
<211> LENGTH: 20
<212> TYPE: DNA
<213> ORGANISM: Homo sapiens

<400> SEQUENCE: 7
gtggaatgtg tgtgagctgg                                               20

<210> SEQ ID NO 8
<211> LENGTH: 20
<212> TYPE: DNA
<213> ORGANISM: Homo sapiens

<400> SEQUENCE: 8
atagggtccg tgcaccattc                                               20

<210> SEQ ID NO 9
<211> LENGTH: 20
<212> TYPE: DNA
<213> ORGANISM: Homo sapiens

<400> SEQUENCE: 9
atgctgagct aaccaccctt                                               20

<210> SEQ ID NO 10
<211> LENGTH: 23
<212> TYPE: DNA
<213> ORGANISM: Homo sapiens

<400> SEQUENCE: 10
aatctttctg ttctgttggc att                                           23

<210> SEQ ID NO 11
<211> LENGTH: 20
<212> TYPE: DNA
<213> ORGANISM: Homo sapiens

<400> SEQUENCE: 11
ctggactgat ctgggctagg                                               20
```

AUTOMATED EXPOSITION OF KNOWN AND NOVEL MULTIPLE MYELOMA GENOMIC VARIANTS USING A SINGLE SEQUENCING PLATFORM

CROSS REFERENCE TO RELATED APPLICATIONS

This application claims benefit of and priority to U.S. Provisional Application 62/418,049, filed Nov. 4, 2016. U.S. Provisional Application 62/418,049 is hereby incorporated by reference in its entirety.

REFERENCE TO A SEQUENCE LISTING

The Sequence Listing, which is a part of the present disclosure, includes a text file comprising primer nucleotide and/or amino acid sequences of the present invention. The subject matter of the Sequence Listing is incorporated herein by reference in its entirety. The information recorded in computer readable form is identical to the written sequence listing.

REFERENCE TO ELECTRONIC TABLES

The Tables, which are a part of the present disclosure, include a text file comprising tables of the present invention. The subject matter of the Tables are incorporated herein by reference each in its entirety.

LENGTHY TABLES

The patent contains a lengthy table section. A copy of the table is available in electronic form from the USPTO web site (https://seqdata.uspto.gov/?pageRequest=docDetail&DocID=US11141709B2). An electronic copy of the table will also be available from the USPTO upon request and payment of the fee set forth in 37 CFR 1.19(b)(3).

INTRODUCTION

Multiple myeloma (MM) is a fatal malignancy of mature plasma B cells. Overt MM is preceded by a premalignant phase, monoclonal gammopathy of undetermined significance (MGUS), which can progress to smoldering MM and ultimately to fatal myeloma. Genetic alterations detected in premalignant MGUS cells are likely initiating events. These may be divided into two primary subtypes that are most often non-overlapping (Manier, S., et al., Nat. Rev. Clin. Oncol., 2012, 14, 100-113): hyperdiploid (HRD) myeloma is characterized by trisomies of most odd-numbered chromosomes (Morgan, G. J., et al., Nat Rev Cancer, 2012, 12, 335-348), while non-HRD myeloma frequently involves immunoglobulin heavy chain (IGH) translocations. These upregulate target oncogenes by placing them under the control of one or both of the powerful, B-cell-specific IGH enhancer regions; canonical IGH partner genes include WHSC1/FGFR3, CCND3, CCND1, MAF, and MAFB in translocations t(4;14), t(6;14), t(11;14), t(14;16), t(14;20), respectively (Manier, S., et al., Nat Rev Clin Oncol., 2012, 14, 100-113). Secondary genetic events are detected in MM, but not its precursor phases, and are thought to drive disease progression. The most prevalent secondary events include MYC translocations (juxtaposing IGH and other loci), single nucleotide variants (SNVs) involving KRAS, NRAS, and DIS3, and copy number variants (CNVs) that amplify chromosome arm 1q or delete 1p, 6q, 13, 14q, or 16q (Morgan, G. J., et al., Nat. Rev. Cancer, 2012, 12, 335-348).

This diversity of genetic lesions has recently been leveraged in a prognostic model that integrates the International Staging System (ISS; Greipp, P. R., et al., J. Clin. Oncol., 2005, 23, 3412-3420), with incidence of CNVs, SNVs, and translocations (Walker, B. A., et al., J. Clin. Oncol., 2015, 33, 3911-3920). This ISS-MUT model increases precision over ISS alone in detecting early mortality and progression. Other studies have highlighted the context-dependent prognostic significance of variants across the spectrum of mutation types (Manier, S., et al., Nat Rev Clin Oncol., 2012, 14, 100-113). For example, trisomies of chromosomes 3 or 5 have been found to abrogate the poor overall survival associated with t(4;14) translocations (Chretien, M. L., et al., Blood, 2015, 126, 2713-2719). Collectively, these results highlight the prognostic impact of the interplay between CNVs, SNVs, and translocations (Morgan, G. J., et al., Nat. Rev. Cancer, 2012, 12, 335-348).

Detecting myeloma-relevant mutations can be accomplished via exome sequencing, as in the ISS-MUT study (Walker, B. A., et al., J. Clin. Oncol., 2015, 33, 3911-3920). However, approaches targeting a subset of disease-associated genes may reduce computational analysis, facilitate quicker return of clinical results, and enable deeper sequencing at a fixed budget (Kortuem, K. M., et al., Br. J. Haematol., 2015, 168, 507-510). Indeed, targeted, clinical sequencing is performed with increasing frequency both commercially (Frampton, G. M., et al., Nat. Biotechnol., 2013, 388, 31, 1023-1031), and through cancer centers (Cheng, D. T., et al., J. Mol. Diagn., 2015, 17, 251-264; Cottrell, C. E., et al., J. Mol. Diagn., 2014, 16, 89-105; Garofalo, A., et al., Genome Med., 2016, 8, 79). In the specific context of MM, an amplicon-based, 77-gene panel detects both CNVs and SNVs (Kortuem, K. M., et al., Blood Cancer J., 2016, 6, e397). This extends an earlier panel (Kortuem, K. M., et al., Br. J. Haematol., 2015, 168, 507-510) used to track mutation evolution across 47 genes (Kortuem, K. M., et al., Ann. Hematol., 2015, 94, 1205-1211). Other efforts have focused on IGH re-arrangements and translocations: amplicon-based sequencing of the locus effectively detects minimal residual disease (Martinez-Lopez, J., et al., Blood, 2014, 123, 3073-3079), while capture-based approaches have been used to discover IGH and MYC translocations (Walker, B. A., et al. Blood Cancer J. 2014, 14, 13; Walker, B. A., et al., Blood, 2013, 121, 3413-3419). A platform was recently described that involves targeted sequencing of the IGH locus and 246 genes implicated in MM and/or other cancers (Bolli, N., et al., Blood Cancer J., 2016, 6, e467). The platform was used to profile 14 MM cell lines and five primary samples. Other attempts to identify genes relevant for MM by exome sequencing include Chapman, M. A., et al., Nature, 2011, 471, 467-472 and Bolli, N., et al., Nat. Commun., 2014, 5, 2997.

SUMMARY

To meet the need to detect myeloma-relevant mutations, the inventors have developed a capture-based sequencing approach that targets multiple myeloma. This approach is capable of simultaneously detecting single nucleotide variants (SNVs), copy number variants (CNVs), and translocations in multiple myeloma (MM). The approach can reduce the amount of sequencing, and hence reduce the amount of time, required to analyze the genome of a patient with multiple myeloma compared to existing methods. In various embodiments, personalized tumor mutations can be identified using sequencing at a depth of no more than 500×, and can be as low as 100×, with optimal efficiency achieved at a sequencing depth of about 300×.

In various embodiments, methods of the present teachings can be used to develop personalized treatment plans for Multiple Myeloma patients based upon the tumor mutations identified.

The inventors have designed oligonucleotide probes that hybridize under stringent conditions to the coding regions (including exons, UTRs, and splice sites) of 467 genes expressed in myeloma. The genes have been selected based on the following criteria (1) are annotated as cancer genes [in COSMIC (Forbes, S. A., et al., Nucleic Acids Res., 2015, 43(Database issue), D805-811) or MutSig (Lawrence, M. S., et al., Nature, 2013, 499(7457), 214-218)], (2) function in DNA repair or B cell biology, (3) are mutated at a frequency of >3% (Chapman, M. A., et al., Nature, 2011, 471, 467-472, Bolli, N., et al., Nat. Commun., 2014, 5, 2997), or (4) have mutations that cluster in hotspots in multiple myeloma tumors.

In various embodiments, the platform was also designed to enable discovery: (1) The inventors queried 465 genes, a much larger set than assayed by previous targeted platforms (Kourtum, K. M., et al., Br. J. Haematol., 2015, 168, 507-510; Kortuem, K. M., et al., Blood Cancer J., 2016, 6, e397; Bolli, N., et al., Blood Cancer J., 2016, 6, e467) and (2) they tiled across the entire V, D, and J regions, as opposed to restricting probes to annotated segments within these regions (Walker, B. A., et al., Blood, 2013, 121, 3413-3419) in order to detect translocations involving inter-segment regions of the locus.

In various configurations, these methods include a) preparing a DNA sequencing library from the genomic DNA obtained from tumor cells of a subject, b) preparing a DNA sequencing library from genomic DNA obtained from non-tumor cells of the subject, c) providing a set of biotinylated oligonucleotide probes for at least 400 genes immobilized thereon, wherein each probe specifically hybridizes to a gene that exhibits at least one single nucleotide variant (SNV), at least one copy number variant (CNV), at least one translocation, or a combination thereof in multiple myeloma, d) hybridizing the sequencing library from the genomic DNA obtained from the tumor to the DNA capture array, e) sequencing the library from the genomic DNA obtained from the tumor cells to a maximum average depth of 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410×415×, 420×, 425×, 430×, 435×, 440×, 445×, 450×, 455×, 460×, 465×, 470×, 475×, 480×, 485×, 490×, 495×, or 500×, f) hybridizing the sequencing library from the genomic DNA obtained from the non-tumor cells to the DNA capture array; g) sequencing the library from the genomic DNA obtained from the non-tumor cells to a maximum average depth of 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410×415×, 420×, 425×, 430×, 435×, 440×, 445×, 450×, 455×, 460×, 465×, 470×, 475×, 480×, 485×, 490×, 495×, or 500×, and h) identifying variants in the genomic DNA obtained from the tumor cells compared to the genomic DNA obtained from the non-tumor cells, thereby identifying somatic mutations in multiple myeloma in the subject. In various configurations, the hybridizing can further comprise purifying the hybridized DNA using streptavidin-labeled magnetic beads.

In various embodiments, the present teachings include methods of identifying multiple myeloma mutations in a subject in need thereof. In various configurations, these methods include a) preparing a DNA sequencing library from the genomic DNA obtained from tumor cells of a subject, b) preparing a DNA sequencing library from genomic DNA obtained from non-tumor cells of the subject, c) providing a DNA capture array comprising a solid support and a set of oligonucleotide probes for detecting at least 400 genes immobilized thereon, wherein each probe specifically hybridizes to a gene that exhibits at least one single nucleotide variant (SNV), at least one copy number variant (CNV), at least one translocation, or a combination thereof in multiple myeloma, d) hybridizing the sequencing library from the genomic DNA obtained from the tumor to the DNA capture array, e) sequencing the library from the genomic DNA obtained from the tumor cells to a maximum average depth of 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410×415×, 420×, 425×, 430×, 435×, 440×, 445×, 450×, 455×, 460×, 465×, 470×, 475×, 480×, 485×, 490×, 495×, or 500×, f) hybridizing the sequencing library from the genomic DNA obtained from the non-tumor cells to the DNA capture array; g) sequencing the library from the genomic DNA obtained from the non-tumor cells to a maximum average depth of 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410×415×, 420×, 425×, 430×, 435×, 440×, 445×, 450×, 455×, 460×, 465×, 470×, 475×, 480×, 485×, 490×, 495×, or 500×, f) hybridizing the sequencing library from the genomic DNA obtained from the non-tumor cells to the DNA capture array; g) sequencing the library from the genomic DNA obtained from the non-tumor cells to a maximum average depth of 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410×415×, 420×, 425×, 430×, 435×, 440×, 445×, 450×, 455×, 460×, 465×, 470×, 475×, 480×, 485×, 490×, 495×, or 500×; and h) identifying variants in the genomic DNA obtained from the tumor cells compared to the genomic DNA obtained from the non-tumor cells, thereby identifying somatic mutations in multiple myeloma in the subject.

In various configurations, these methods include a) preparing a DNA sequencing library from the genomic DNA obtained from tumor cells of a subject, b) preparing a DNA sequencing library from genomic DNA obtained from non-tumor cells of the subject, c) providing a DNA capture array comprising a solid support and oligonucleotide probes immobilized thereon for detecting at least 400 genes or a set of biotinylated oligonucleotide probes in solution for detecting at least 400 genes, wherein each probe specifically hybridizes to a gene that exhibits at least one single nucleotide variant (SNV), at least one copy number variant (CNV), at least one translocation, or a combination thereof in multiple myeloma, d) hybridizing the sequencing library from the genomic DNA obtained from the tumor to the DNA capture array, e) sequencing the library from the genomic DNA obtained from the tumor cells to a maximum average depth of 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410×415×, 420×, 425×, 430×, 435×, 440×, 445×, 450×, 455×, 460×, 465×, 470×, 475×, 480×, 485×, 490×, 495×, or 500×, f) hybridizing the sequencing library from the genomic DNA obtained from the non-tumor cells to the DNA capture array; g) sequencing the library from the genomic DNA obtained from the non-tumor cells to a maximum average depth of 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 330325×, 335×, 340×, 345×, 350×, 355×, 360×, 365×, 370×, 380×, 385×, 390×, 400×, 405×, 410×415×, 420×, 425×, 430×, 435×, 440×, 445×, 450×, 455×, 460×, 465×, 470×, 475×, 480×, 485×, 490×, 495×, or 500×, and h) identifying variants in the genomic DNA obtained from the tumor cells compared to the genomic DNA obtained from the non-tumor cells, thereby identifying somatic mutations in multiple myeloma in the subject.

In various configurations, the at least 400 genes can comprise, consist essentially of, or consist of 467 genes which are mutated in multiple myeloma.

In various configurations, the at least 400 genes can comprise, consist essentially of, or consist of 465 genes which are mutated in multiple myeloma.

In various configurations, the at least 400 genes can comprise, consist essentially of, or consist of less than 500 genes which are mutated in multiple myeloma.

In various configurations, the at least 400 genes can comprise, consist essentially of, or consist of DTNB, DNMT3A, ULK4, TRAK1, DNAH11, CDCA7L, FGFR3, WHSC1, CCND3, CCND1, MAF, MAFB, CKS1B, ANP32E, LTBR, MAP4K4, MYC, CDKN2C, RB1, CDKN2A, NRAS, KRAS, BRAF, PIK3CA, AKT1, TRAF3, CYLD, DKK1, FRZB, DNAH5, XBP1P1, PRDM1, IRF4, TP53, MRE11A, PARP1, DIS3, FAM46C, LRRK2, KDM6A, MLL, HOXA9, KDM6B, FAF1, BIRC2, BIRC3, WWOX, ACTG1, FNDC3A, MAX, TNKS, RPL10, BCL7A, EGR1, SP140, GCET2, HIST1H3G, SNRNP48, BAGE2, MEOX1, FERMT2, PRND, TRIP12, DNAH2, RASA2, PLA2G2D, COBLL1, ATF7IP, GSTO2, SLC24A1, AASS, RBM25, ROBO2, THRAP3, ZNF326, GNG7, IFI44, STARD13, HAUS3, TTC7B, CDKN1B, RNF151, SLC36A1, FAM153B, OR1L8, PRUNE2, COL4A1, USP50, SAMHD1, CXCR4, CHD2, KRTDAP, PTCH2, FBXO36, ABCC4, UBB, YTHDF2, HUWE1, NLRC5, CDH8, PHOX2B, CDCA2, MOGAT3, PSMD1, EXOG, GRIA2, CCDC144NL, IQSEC1, CKM, SYMPK, DAAM1, PTPRZ1, OR1N2, AGTR2, DUSP28, ADCY8, ACACA, PRIM2, DOLK, CST4, ACSM4, TMCO3, HTR6, OR1S2, NDUFAF3, FAM122C, SLC48A1, HIST1H3H, PNRC1, NALCN, COL11A2, LCE3A, ZNF431, HERC4, TMEM143, CDC27, FXYD6, OR5P3, MALL, PLXDC2, EGFL6, CELSR2, PHKB, IRX2, PRKD2, STX5, TOM1L1, COX7B2, RNF40, PTPRD, MMP7, YAP1, MSRA, KIAA1377, SOX7, FAM167A, RP1L1, XKR6, CSMD2, PDE4DIP, FLG, HMCN1, RGS2, USH2A, OBSCN, RYR2, ANK3, TACC2, MKI67, LRRC4C, FAT3, DYNC2H1, BTG1, EP400, AHNAK2, RYR3, HYDIN, ZFHX3, DNAH9, LAMA1, ZNF208, ZNF257, RYR1, FCGBP, NRXN1, NEB, SCN2A, FRG1B, BSN, ROBO1, KALRN, ANK2, FAT14, TRIO, FAM134B, MYO10, CMYA5, VCAN, FBN2, PKHD1, DST, SYNE1, HECW1, PCLO, PCMTD1, ZFHX4, CSMD3, MLLT3, TRPM3, GJB3, KTI12, DIRAS3, HIST2H3D, HIST2H2BE, HIST2H2AC, HIST3H2A, NAMPTL, RBMXL2, CDC42EP2, KRTAP5-10, FUT4, HIST4H4, ATXN7L3B, PABPC3, SPRY2, GREM1, EID1, IMP3, SOCS1, NACA2, TRAPPC5, RPS28, ZNF493, RPSAP58, FFAR2, EID2B, FAM84A, FOXD4L1, TMEM177, KCNE4, MOV10L1, LRRC3B, RPP14, CGGBP1, H1FX, SLC35G2, CRIPAK, DCAF16, PURA, HIST1H4B, HIST1H2BB, HIST1H3C, HIST1H1C, HIST1H4C, HIST1H2AC, HIST1H1E, HIST1H3E, HIST1H3D, HIST1H2BF, HIST1H4E, HIST1H2AE, HIST1H1D, HIST1H3F, HIST1H4H, HIST1H2BJ, HIST1H2AG, HIST1H2BK, HIST1H2BL, HIST1H2BM, HIST1H2AM, HIST1H2BO, LTB, C2, TBCC, TPBG, CLDN4, PEG10, RNF133, NAT1, AQP7, GCNT1, DIRAS2, TMSB4X, CPXCR1, RPA4, TCEAL3, MAGEC3, NOTCH2, EHD1, AKAP6, LRRTM4, VCPIP1, ABCA2, LYPLA2, DTX1, MYOM1, TGFB1, RRBP1, RPRD1B, IGLL5, ZNF148, RNF150, ATM, ARID2, SCAF11, WDR87, SETD2, EXOC4, MAGED1, SLIT3, SLC6A11, ZNF319, ZNF100, ZNF91, ZNF681, ZNF235, ZNF616, ZNF721, KCNH4, GRM7, TJP3, FMN1, TLR5, VDR, ADRA2B, LRRN1, SLIT2, ATR, AICDA, SUPT5H, UNG, CCDC88A, MSH2, NLRP2, PAX5, TCF3, ID2, NFKB1, NFKB2, RELA, PRKACB, PTBP2, APEX1, APEX2, MSH6, TRIM28, SUPT6H, MSH3, MSH5, POLQ, RNF8, RNF168, REV3L, PMS2, PAXIP1, PCNA, MLH1, MLH3, EXO1, XRCC6, XRCC5, LIG4, XRCC4, PRKDC, DCLRE1C, NHEJ1, NBN, RAD50, RBBP8, LIG3, LIG1, XRCC1, BBC3, BCL2L11, PRKCD, BCL2L1, TNFSF13B, RAG1, RAG2, H2AFX, MDC1, TP53BP1, CHEK2, BLM, RIF1, SAMSN1, LILRB3, U2AF1, SF3B1, SRSF2, NADK, DNAJC11, DENND4B, KCNN3, ARHGEF11, CR1, KIF26B, AGAP5, TMEM216, TECTA, ZCRB1, CLIP1, UPF3A. SYNRG, PNKP, IDH1, RALGAPA2, NCOA6, CTCFL, EFCAB6, TOMM70A, INTS12, ANKHD1, ZNF318, PLG, TBP, CNTNAP2, ANKRD18B3, PCSK5, SHC3, DDX11, HLA-A, HLA-DRB1, ISPD, ALK, ANTXR2, ARID1A, AXL, BAI2, BCORL1, BRCA2, CARD11, CCDC155, CDHR1, CHD3, CNKSR2, DCLK2, DICER1, HOXA4, IGF1R, IKBKB, IL6ST, JAK2, KIT, MED12, MED12L, MERTK, MLL5, MTOR, NBEA, NOTCH1, PIK3C2G, PIM1, PTPN11, PTPN14, ROS1, SKP2, SPOP, ST7, STAT3, TP63, TPTE, XBP1, ZIM3, and ZNF717.

In various configurations, an array or set of oligonucleotides can include probes that be tiled in an unbiased fashion from ~50 Kb upstream to ~50 Kb downstream of the IgH locus. In some configurations, probes which can be tiled in an unbiased fashion from ~50 Kb upstream to ~50 Kb downstream of the IgH locus can comprise, consist essentially of, or consist of probes which can hybridize within one or more of the variable (IGHV), diversity (IGHD), joining (IGHJ), and constant/switch regions of the IgH locus. In various configurations, probes of an array or set of oligonucleotides can comprise probes that can target an exonic region of a canonical IGH translocation partner, which can comprise, consist essentially of, or consist of CCND1, CCND3, FGFR3, MAF, MAFB, WHSC1, WWOX or a combination thereof.

In various configurations, an array or set of oligonucleotides can include probes that can be tiled across exonic and intronic regions of the MYC locus, spanning from ~50 Kb upstream to ~100 Kb downstream.

In various configurations, an array or set of oligonucleotides can comprise oligonucleotide probes that can hybridize to NRAS, KRAS, FAM46C, TP53, DIS3, IGLL5 and BRAF.

In various configurations, an array or set of oligonucleotides can comprise oligonucleotide probes that can hybridize to ATM, BRCA2, CARD11, CCND1, CCND3, CYLD, DIS3, DNAH5, DNAH11, DNMT3A, FAM46C, FGFR3, JAK2, KDM6A, KDM6B, KIT, KRAS, MAF, MAFB, MTOR, MYC, NFKB1, NOTCH1, NOTCH2, PARP1, RB1, TRAF3, and WHSC1.

In various configurations, an array or set of oligonucleotides can include oligonucleotide probes that can hybridize to CLIP1, CSMD3, EP400, FMN1, FRG1B, KDM6A, KRAS, LAMA1, MLLT3, MSH2, MSH6, NOTCH1, OR1S2, PAX5, and RB1. In various configurations, an array or set of oligonucleotides can comprise, consist of, or consist essentially of probes that hybridize to CLIP1, CSMD3, EP400, FMN1, FRG1B, KDM6A, KRAS, LAMA1, MLLT3, MSH2, MSH6, NOTCH1, OR1S2, PAX5, and RB1.

In various embodiments, the present teachings include a DNA capture array comprising a solid support and oligonucleotide probes immobilized thereon for detecting at least 400 genes, wherein each probe hybridizes a gene that exhibits at least one single nucleotide variant (SNV), at least one copy number variant (CNV), at least one translocation, or a combination thereof in a myeloma tumor cell in multiple myeloma.

In various embodiments, a DNA capture array can comprise, consist of, or consist essentially of a set of biotinylated oligonucleotide probes for detecting at least 400 genes, wherein each probe hybridizes to a genomic region that exhibits at least one single nucleotide variant (SNV), at least one copy number variant (CNV), at least one translocation, or a combination thereof in a myeloma tumor cell in multiple myeloma.

In various embodiments, a DNA capture array of the present teachings can comprise, consist of, or consist essentially of a solid support and at least 400 oligonucleotide probes immobilized thereon, wherein each probe hybridizes a gene that exhibits at least one single nucleotide variant (SNV), at least one copy number variant (CNV), at least one translocation, or a combination thereof in multiple myeloma.

In some configurations, the oligonucleotide probes comprise a plurality of probes which are tiled in an unbiased fashion from ~50 Kb upstream to ~50 Kb downstream of the IgH locus. In various configurations, the plurality of probes which are tiled in an unbiased fashion from ~50 Kb upstream to ~50 Kb downstream of the IgH locus include probes which hybridize within one or more of the variable (IGHV), diversity (IGHD), joining (IGHJ), and constant/switch regions.

In various configurations, the array can comprise, consist of, or consist essentially of one or more probes which target an exonic region of a canonical IGH translocation partner. In various configurations, the canonical IGH translocation partner can be CCND1, CCND3, FGFR3, MAF, MAFB, WHSC1, WWOX or a combination thereof.

In various configurations, the oligonucleotide probes can comprise a plurality of probes which are tiled across exonic and intronic regions of the MYC locus, spanning from ~50 Kb upstream to ~100 Kb downstream of the MYC locus.

In various configurations, the plurality of oligonucleotide probes can include probes that hybridize to NRAS, KRAS, FAM46C, TP53, DIS3, IGLL5, and/or BRAF.

In various configurations, the plurality of oligonucleotide probes can include probes which hybridize to ATM, BRCA2, CARD11, CCND1, CCND3, CYLD, DIS3, DNAH5, DNAH11, DNMT3A, FAM46C, FGFR3, JAK2, KDM6A, KDM6B, KIT, KRAS, MAF, MAFB, MTOR, MYC, NFKB1, NOTCH1, NOTCH2, PARP1, RB1, TRAF3 and/or WHSC1.

In various configurations, the plurality of oligonucleotide probes can include probes that hybridize to CLIP1, CSMD3, EP400, FMN1, FRG1B, KDM6A, KRAS, LAMA1, MLLT3, MSH2, MSH6, NOTCH1, OR1S2, PAX5, and/or RB1.

In various configurations, the at least 400 genes can comprise, consist of, or consist essentially of DTNB, DNMT3A, ULK4, TRAK1, DNAH11, CDCA7L, FGFR3, WHSC1, CCND3, CCND1, MAF, MAFB, CKS1B, ANP32E, LTBR, MAP4K4, MYC, CDKN2C, RB1, CDKN2A, NRAS, KRAS, BRAF, PIK3CA, AKT1, TRAF3, CYLD, DKK1, FRZB, DNAH5, XBP1P1, PRDM1, IRF4, TP53, MRE11A, PARP1, DIS3, FAM46C, LRRK2, KDM6A, MLL, HOXA9, KDM6B, FAF1, BIRC2, BIRC3, WWOX, ACTG1, FNDC3A, MAX, TNKS, RPL10, BCL7A, EGR1, SP140, GCET2, HIST1H3G, SNRNP48, BAGE2, MEOX1, FERMT2, PRND, TRIP12, DNAH2, RASA2, PLA2G2D, COBLL1, ATF7IP, GSTO2, SLC24A1, AASS, RBM25, ROBO2, THRAP3, ZNF326, GNG7, IFI44, STARD13, HAUS3, TTC7B, CDKN1B, RNF151, SLC36A1, FAM153B, OR1L8, PRUNE2, COL4A1, USP50, SAMHD1, CXCR4, CHD2, KRTDAP, PTCH2, FBXO36, ABCC4, UBB, YTHDF2, HUWE1, NLRC5, CDH8, PHOX2B, CDCA2, MOGAT3, PSMD1, EXOG, GRIA2, CCDC144NL, IQSEC1, CKM, SYMPK, DAAM1, PTPRZ1, OR1N2, AGTR2, DUSP28, ADCY8, ACACA, PRIM2, DOLK, CST4, ACSM4, TMCO3, HTR6, OR1S2, NDUFAF3, FAM122C, SLC48A1, HIST1H3H, PNRC1, NALCN, COL11A2, LCE3A, ZNF431, HERC4, TMEM143, CDC27, FXYD6, OR5P3, MALL, PLXDC2, EGFL6, CELSR2, PHKB, IRX2, PRKD2, STX5, TOM1L1, COX7B2, RNF40, PTPRD, MMP7, YAP1, MSRA, KIAA1377, SOX7, FAM167A, RP1L1, XKR6, CSMD2, PDE4DIP, FLG, HMCN1, RGS2, USH2A, OBSCN, RYR2, ANK3, TACC2, MKI67, LRRC4C, FAT3, DYNC2H1, BTG1, EP400, AHNAK2, RYR3, HYDIN, ZFHX3, DNAH9, LAMA1, ZNF208, ZNF257, RYR1, FCGBP, NRXN1, NEB, SCN2A, FRG1B, BSN, ROBO1, KALRN, ANK2, FAT4, TRIO, FAM134B, MYO10, CMYA5, VCAN, FBN2, PKHD1, DST, SYNE1, HECW1, PCLO, PCMTD1, ZFHX4, CSMD3, MLLT3, TRPM3, GJB3, KTI12, DIRAS3, HIST1H3D, HIST2H2BE, HIST2H2AC, HIST3H2A, NAMPTL, RBMXL2, CDC42EP2, KRTAP5-10, FUT4, HIST4H4, ATXN7L3B, PABPC3, SPRY2, GREM1, EDI1, IMP3, SOCS1, NACA2, TRAPPC5, RPS28, ZNF493, RPSAP58, FFAR2, EID2B, FAM84A, FOXD4L1, TMEM177, KCNE4, MOV10L1, LRRC3B, RPP14, CGGBP1, H1FX, SLC35G2, CRIPAK, DCAF16, PURA, HIST1H4B, HIST1H2BB, HIST1H3C, HIST1H1C, HIST1H4C, HIST1H2AC, HIST1H1E, HIST1H3E, HIST1H3D, HIST1H2BF, HIST1H4E, HIST1H2AE, HIST1H1D, HIST1H3F, HIST1H4H, HIST1H2BJ, HIST1H2AG, HIST1H2BK, HIST1H2BL, HIST1H2BM, HIST1H2AM, HIST1H2BO, LTB, C2, TBCC, TPBG, CLDN4, PEG10, RNF133, NAT1, AQP7, GCNT1, DIRAS2, TMSB4X, CPXCR1, RPA4, TCEAL3, MAGEC3, NOTCH2, EHD1, AKAP6, LRRTM4, VCPIP1, ABCA2, LYPLA2, DTX1, MYOM1, TGFB1, RRBP1, RPRD1B, IGLL5, ZNF148, RNF150, ATM, ARID2, SCAF11, WDR87, SETD2, EXOC4, MAGED1, SLIT3, SLC6A11, ZNF319, ZNF100, ZNF91, ZNF681, ZNF235, ZNF616, ZNF721, KCNH4, GRM7, TJP3, FMN1, TLR5, VDR, ADRA2B, LRRN1, SLIT2, ATR, AICDA, SUPT5H, UNG, CCDC88A, MSH2, NLRP2, PAX5, TCF3, ID2, NFKB1, NFKB2, RELA, PRKACB, PTBP2, APEX1, APEX2, MSH6, TRIM28, SUPT6H, MSH3, MSH5, POLQ, RNF8, RNF168, REV3L, PMS2, PAXIP1, PCNA, MLH1, MLH3, EXO1, XRCC6, XRCC5, LIG4, XRCC4, PRKDC, DCLRE1C, NHEJ1, NBN, RAD50, RBBP8, LIG3, LIG1, XRCC1, BBC3, BCL2L11, PRKCD, BCL2L1, TNFSF13B, RAG1, RAG2, H2AFX, MDC1, TP53BP1, CHEK2, BLM, RIF1, SAMSN1, LILRB3, U2AF1, SF3B1, SRSF2, NADK, DNAJC11, DENND4B, KCNN3, ARHGEF11, CR1, KIF26B, AGAP5, TMEM216, TECTA, ZCRB1, CLIP1, UPF3A, SYNRG, PNKP, IDH1, RALGAPA2, NCOA6, CTCFL, EFCAB6, TOMM70A, INTS12, ANKHD1, ZNF318, PLG, TBP, CNTNAP2, ANKRD18B, PCSK5, SHC3, DDX11, HLA-A, HLA-DRB1, ISPD, ALK, ANTXR2, ARID1A, AXL, BAI2, BCORL1, BRCA2, CARD11, CCDC155, CDHR1, CHD3, CNKSR2, DCLK2, DICER1, HOXA4, IGF1R, IKBKB, IL6ST, JAK2, KIT, MED12, MED12L, MERTK, MLL5, MTOR, NBEA, NOTCH1, PIK3C2G, PIM1, PTPN1, PTPN14, ROS1, SKP2, SPOP, ST7, STAT3, TP63, TPTE, XBP1, ZIM3, and ZNF717.

In various configurations, the at least 400 genes can be 465 genes.

In various configurations, the at least 400 genes can be 467 genes.

In various configurations, the at least 400 genes can be less than 500 genes.

In various configurations, the at least 400 genes can be at least 401, at least 402, at least 403, at least 404, at least 405, at least 406, at least 407, at least 408, at least 409, at least 410, at least 411, at least 412, at least 413, at least 414, at least 415, at least 416, at least 417, at least 418, at least 419, at least 420, at least 421, at least 422, at least 423, at least 424, at least 425, at least 426, at least 427, at least 428, at least 429, at least 430, at least 431, at least 432, at least 433, at least 434, at least 435, at least 436, at least 437, at least 438, at least 439, at least 440, at least 441, at least 442, at least 443, at least 444, at least 445, at least 446, at least 447, at least 448, at least 449, at least 450, at least 451, at least 452, at least 453, at least 454, at least 455, at least 456, at least 457, at least 458, at least 459, at least 460, at least 461, at least 462, at least 463, at least 464, at least 465, at least 466, at least 467, at least 468, at least 469, at least 470, at least 471, at least 472, at least 473, at least 474, at least 475, at least 476, at least 477, at least 478, at least 479, at least 480, at least 481, at least 482, at least 483, at least 484, at least 485, at least 486, at least 487, at least 488, at least 489, at least 490, at least 491, at least 492, at least 493, at least 494, at least 495, at least 496, at least 497, at least 498, at least 499, or 500 genes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates VAF (y axis) density (x axis) of exome-specific variants.

DETAILED DESCRIPTION

Figure 1:
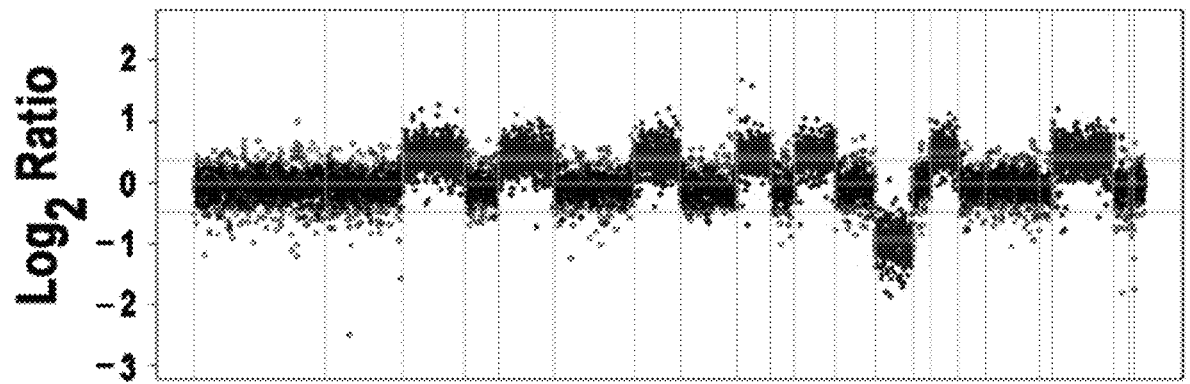
FIG. 1 illustrates identification by targeted sequencing of chromosome-level, arm-level, and focal CNVs in hyperdiploid events detected by CopyCat2 (blue; $p<0.05$) from $\log_2$ ratios of tumor to paired normal sequencing depth (y axis) across chromosomes (x axis).

The present inventors have developed a DNA capture array comprising biotinylated oligonucleotide probes or a solid support and oligonucleotide probes immobilized thereon. An array can detect at least 400 genes, wherein each probe hybridizes a gene that exhibits at least one single nucleotide variant (SNV), at least one copy number variant (CNV), at least one translocation, or a combination thereof in a myeloma tumor cell in multiple myeloma.

As used herein, an oligonucleotide probe that specifically hybridizes a gene refers to oligonucleotides that are tiled across a genomic region for a specific gene or gene region and can include an oligonucleotide that binds coding sequence, introns, or flanking regions of the targeted gene.

In various embodiments, the present teachings include methods of identifying multiple myeloma mutations in a subject in need thereof. In various configurations, these methods include a) preparing a DNA sequencing library from the genomic DNA obtained from tumor cells of a subject, b) preparing a DNA sequencing library from genomic DNA obtained from non-tumor cells of the subject, c) providing a DNA capture array comprising a solid support and a set of oligonucleotide probes for detecting at least 400 genes immobilized thereon, wherein each probe specifically hybridizes to a gene that exhibits at least one single nucleotide variant (SNV), at least one copy number variant (CNV), at least one translocation, or a combination thereof in multiple myeloma, d) hybridizing the sequencing library from the genomic DNA obtained from the tumor to the DNA capture array, e) sequencing the library from the genomic DNA obtained from the tumor cells to a maximum average depth of, e.g., 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410× 415×, 420×, 425×, 430×, 435×, 440×, 445×, 450×, 455×, 460×, 465×, 470×, 475×, 480×, 485×, 490×, 495×, or 500×; f) hybridizing the sequencing library from the genomic DNA obtained from the non-tumor cells to the DNA capture array; g) sequencing the library from the genomic DNA obtained from the non-tumor cells to a maximum average depth of 100×, 105×, 110×, 110×, 5×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410× 415×, 420×, 425×, 430×, 435×, 440×, 445×, 450×, 455×, 460×, 465×, 470×, 475×, 480×, 485×, 490×, 495×, or 500×; and h) identifying variants in the genomic DNA obtained from the tumor cells compared to the genomic DNA obtained from the non-tumor cells, thereby identifying somatic mutations in multiple myeloma in the subject.

In various embodiments, the present teachings include methods of identifying multiple myeloma mutations in a subject in need thereof. In various configurations, these methods include a) preparing a DNA sequencing library from the genomic DNA obtained from tumor cells of a subject, b) preparing a DNA sequencing library from genomic DNA obtained from non-tumor cells of the subject, c) providing a DNA capture array comprising biotinylated oligonucleotide probes for detecting at least 400 genes, wherein each probe specifically hybridizes to a gene that exhibits at least one single nucleotide variant (SNV), at least one copy number variant (CNV), at least one translocation, or a combination thereof in multiple myeloma, d) hybridizing the sequencing library from the genomic DNA obtained from the tumor to the DNA capture array, e) sequencing the library from the genomic DNA obtained from the tumor cells to a maximum average depth of, e.g., 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410×, 415×, 420×, 425×, 430×, 435×, 440×, 445×, 450×, 455×, 460×, 465×, 470×, 475×, 480×, 485×, 490×, 495×, or 500×; f) hybridizing the sequencing library from the genomic DNA obtained from the non-tumor cells to the DNA capture array; g) sequencing the library from the genomic DNA obtained from the non-tumor cells to a maximum average depth of 100×, 105×, 110×, 115×, 120×, 125×, 130×, 135×, 140×, 145×, 150×, 155×, 160×, 165×, 170×, 175×, 180×, 185×, 190×, 195×, 200×, 205×, 210×, 215×, 220×, 225×, 230×, 235×, 240×, 245×, 250×, 255×, 260×, 265×, 270×, 275×, 280×, 285×, 290×, 295×, 300×, 305×, 310×, 315×, 320×, 325×, 330×, 335×, 340×, 345×, 350×, 355×, 360×, 365×, 370×, 380×, 385×, 390×, 400×, 405×, 410×415×, 420×, 425×, 430×, 435×, 440×, 445×, 450×, 455×, 460×, 465×, 470×, 475×, 480×, 485×, 490×, 495×, or 500×; and h) identifying variants in the genomic DNA obtained from the tumor cells compared to the genomic DNA obtained from the non-tumor cells, thereby identifying somatic mutations in multiple myeloma in the subject.

In various configurations, the arrays and methods of use of the present teachings allow for assays for multiple myeloma that can be more rapid and more cost-effective compared to whole-exome sequencing. Assays performed by the disclosed methods can also be sufficiently comprehensive to detect infrequently-occurring variants.

In some configurations, methods and arrays of the present teachings can be used to detect single nucleotide variants, copy number changes, and translocations in multiple myeloma. In some configurations, data capture using an array of the present teachings can be less expensive and faster than current clinical analysis systems and methods such as I-FISH. Furthermore, data capture using an array of the present teachings can include automation of copy number calling.

In various configurations, analysis of tumor mutations in an individual MM patient, including identification of SNVs, CNVs and translocations, can be used to determine the patient's prognosis and to monitor disease progression, and can also be used to select an appropriate therapy for the patient.

In some configurations, methods developed by the inventors can be combined with gene expression profiling (Weinhold, N., et al., Leukemia, 2016, 30(2), 423-430). Comparing this array to existing technology, the custom capture of the present teachings can include from about 400 to about 500 genes, for example 400, 405, 410, 415, 420, 425, 430, 435, 440, 445, 450, 455, 460, 465, 470, 475, 480, 485, 490, 495, or 500 genes (as opposed to, e.g., 60).

In some configurations, the present teachings include methods of determining mutual exclusivity/co-occurrence of Multiple Myeloma over the entire population. For example and without limitation, in some configurations, one can test mutual exclusivity of NRAS, KRAS, and IGLL5: i. Test for all 3 simultaneously, if possible, otherwise do pairwise comparisons; ii. Make lolliplots (Skidmore, Z. L., et al., Bioinformatics. 2016 Oct. 1; 32(19): 3012-3014) of all 3: include all mutations (including silent mutations, intronic mutations, and those in the up- and down-stream UTRs) in all 3; iii. A MAF (mutation annotation file) file characterizing mutations (in an appropriate format) can include unfiltered NRAS, KRAS, and IGLL5 mutations—i.e., including intronic mutations, silent mutations, and those in the up- and down-stream UTRs.

In various configurations, one can test for mutual exclusivity of hyperdiploid and (non-myc) IGH translocations. These are largely mutually exclusive (but not completely). For example and without limitation, one can treat all non-myc IGH translocations as the same mutation—this can involve adjusting the MAF so that all IGH translocations [i.e., t(4;14), t(11;14), etc.] have the same name/genomic location/etc. [e.g., "t(14)"].

In some configurations, one can test for co-occurrence of other relations between CNA and SNVs noted in the literature. For example, but without limitation, del(1p) is known to be associated with FAM46C mutation (Boyd, K. D., et al., Clin. Cancer Res., 2011, 17(24), 7776-7784), del(13q) associated with DIS3 mutation, del(14q) associated with TRAF3 mutation (Annunziata, C. M., et al., Cancer Cell., 2007, 12(2), 115-130; Keats, J. J., et al., Cancer Cell., 2007, 12(2), 131-144), and del(17p) associated with TP53 mutation (Walker, B. A., et al., Blood, 2010, 116(15), e56-65). In various configurations, one can test for co-occurrence of SNVs and translocations, for example, but without limitation, an FGFR3 mutation can be correlated with t(4;14), but to analyze this, t(4;14) can be treated as distinct from other translocations. Similarly, in various configurations, IGH translocations can be treated as being distinct from one another, for example and without limitation, a DIS3 mutation can be correlated with t(4; 14), an FGFR3 mutation can be correlated with t(4;14), a PRKD2 mutation can be correlated with t(4;14), a KRAS mutation can be correlated with t(11;14), a CCND1 mutation can be correlated with t(11;14), an IRF4 mutation can be correlated t(11;14), a PRDM1 mutation can be correlated with t(14;16), a DIS3 mutation can be correlated t(14;16).

In some configurations, one can test if IGLL5 can co-occur with del(13q). Whole-genome sequencing can reveal activation-induced cytidine deaminase signatures during indolent chronic lymphocytic leukaemia evolution. (Kasar, S., et al., Nat Commun., 2015, 6, 8866).

In various configurations, one can test if IGLL5 co-occur with DNA repair/B-cell mutations. One can treat these as a class by comparing IGLL5 to the entire class of repair/B-cell genes. Presumably, this means treating them as a single mutation/genomic coordinate, similar to the analysis for IGH.

In various configurations, one can test if a gene such as IGLL5 is mutually exclusive or is co-occurring with any other mutation. In various configurations, one can test if there are pairwise relationships, e.g., mutual exclusivity or co-occurrence, between two specified genes.

In various configurations, one can test if there are any pairwise relationships (mutually exclusivity or co-occurrence) between repair and B-cell genes. In various configurations, the B cell genes can comprise AICDA, APEX1, APEX2, ATM, BBC3, BCL2L1, BCL2L11, BLM, CCDC88A, CHEK2, DCLRE1C, DYT10, ERCC1, EXO1, H2AFX, HSP90AA1, ID2, ID3, IL4, LIG3, LIG4, LRIG1, MDC1, MIR155, MIR181B1, MIR181B2, MLH1, MLH3, MRE11A, MSH2, MSH3, MSH4, MSH5, MSH6, NBN, NFKB1, NFKB2, NHEJ1, NLRP2, PARP1, PARP2, PAX5, PAXIP1, PCNA, PMS2, POLB, POLL, POLM, POLQ, PPP2CA, PRKACA, PRKACB, PRKCD, PRKDC, PTBP2, RAD50, RAG1, RAG2, RBBP8, REL, RELA, RELB, REV3L, RFC1, RFC2, RFC3, RFC4, RFC5, RNF168, RNF8, RPA1, RUNX1, RUNX2, RUNX3, SERPINA2P, SMAD3, SMAD4, STAT6, SUPT5H, SUPT6H, TCF3, TGFB1, TNFSF13B, TP53, TP53BP1, TRIM28, UNG, XRCC1, XRCC4, XRCC5, and XRCC6.

In various configurations, one can perform of a mutual exclusivity analysis and co-occurrence between any two mutations, without specifying a priori what those two mutations are.

In some configurations, the present teachings include an integrative analysis.

Methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Methods in Molecular Biology (book series) Humana Press, Clifton N.J.; methods are also described in the product literature for sequencing kits such as the ILLUMINA® TRUSEQ® (Illumina, Inc., San Diego, Calif.) DNA Sample Preparation Guide, ILLUMINA® Part#15036486 Rev. C July 2012. All references cited herein are hereby incorporated by reference, each in its entirety. As used in the present description and any appended claims, the singular forms "a", "an" and "the" are intended to include the plural forms as well, unless the context indicates otherwise.

DETAILED DESCRIPTION

Methods
Custom Capture Sequencing Platform Design

In various embodiments, the following methods can be used for carrying out the methods of the present teachings. The present inventors designed a Nimblegen probe set (Roche) targeting 3.3 Mb of space that includes 465 genes and the IGH region. ~1.3 Mb of the capture space spans the IGH locus and ~160 Kb spans the MYC locus. Probes were designed from ~50 Kb upstream to ~50 Kb downstream of the IGH locus (chr14:105982580—107289508; hg19 coordinates). 85% of this region was nominally covered by probes, though additional coverage was provided by the wingspan of these probes. Probes were also designed across exonic and intronic regions of the MYC locus spanning ~50 Kb upstream to ~100 Kb downstream (chr8:128697680—128853674; hg19 coordinates). 70% of this region was covered by probes. This facilitated detection of chromosome-level, arm-level, and focal copy number alterations. The inventors also designed probes targeting the exonic regions of canonical IGH translocation partners (CCND1, CCND3, FGFR3, MAF, MAFB, WHSC1, and WWOX), but did not design probes within the intronic or nearby intergenic regions of these genes where translocations often occur. Without being limited by theory, it is believed that the IGH (and MYC) probes acted as bait, enriching for molecules that juxtapose a fragment of the IGH (or MYC) locus (complementary to the probe) and the partner gene. Paired-end sequencing then detects the partner gene when: (1) a chimeric (or split) read spans the breakpoint, thus revealing it at nucleotide resolution and/or (2) each of the two mates of the paired-end read align to one of the partners, thus bracketing the breakpoint and defining a region over which it occurred.

Without being limited by theory, the inventors hypothesized that endonucleolytic cleavage of free DNA ends prior to fusion with a partner chromosome could result in translocation breakpoints upstream of the double-stranded break. Hence, even if double-stranded breaks occur at the boundaries or within the IGHV, IGHD, or IGHJ genes or of the switch regions, the translocation breakpoint may not respect these boundaries. As such, the inventors designed probes to lie entirely outside, entirely inside, or partially outside/inside these genomic elements. All chromosomes arms have coverage except 13p, 14p, 15p, 22p, Yp, and Yq. All of these except Yq are tandem-rich arms of acrocentric chromosomes.

Capture Sequencing of 95 Tumor/Normal Pairs

Automated dual indexed libraries were constructed with 100-250 ng of genomic DNA utilizing the KAPA® HTP Library Kit (KAPA Biosystems, Wilmington, Mass.) on the SCICLONE® NGS instrument (Perkin Elmer, Waltham, Mass.) targeting 250 bp inserts. 96 libraries were pooled pre-capture generating a 5 µg library pool. Library pools were hybridized with the biotinylated Nimblegen probe set in solution. The concentration of each captured library pool was accurately determined through qPCR according to the manufacturer's protocol (KAPA Biosystems) to produce cluster counts appropriate for the ILLUMINA® HISEQ® 2000 (Illumina Inc., San Deigo, Calif.) platform. Two lanes of 2×100 sequence data were generated per library pool. One of the original 96 samples was subsequently excluded because of low coverage. Sequencing library pools were prepared, hybridized to the probes, and sequenced on the HiSeq2000 (2×100 reads for initial sequencing of 95 tumor-normal pairs) or the HiSeq2500 (2×125 reads for deep sequencing of a subset of 15 pairs). Reads were aligned against human reference genome GRCh37-lite using BWA (Li, H. and Durbin R., Bioinformatics, 2009, 25, 1754-1760). SNVs were called using samtools (Li, H., et al., Bioinformatics, 2009, 25, 2078-2079), SomaticSniper (Larson, D. E., et al., Bioinformatics, 2012, 28, 311-317), MuTect, (Cibulskis, K., et al., Nat Biotechnol., 2013, 31, 213-219) Strelka (Saunders, C. T., et al., Bioinformatics, 2012, 28, 1811-1817), and VarScan2 (Koboldt, D. C, et al., Genome Res, 2012, 22, 568-576). Translocations were called using LUMPY (Layer, R. M., et al., Genome Biol., 2014, 15, R84), with results filtered by a machine learning approach optimized to achieve high precision relative to available FISH results. CNVs were called using CopyCAT2 (Sehn, J. K., et al., Exp. Mol. Pathol., 2014, 97, 69-73) parameterized to detect copy number alterations exceeding the level of noise estimated from diploid regions using a gaussian mixture model.

Deep Capture Sequencing of 15 Tumor/Normal Pairs

Fifteen tumor/normal pairs (a subset of the original 96 samples sequenced) were subjected to additional sequencing in three batches. Six pairs were subjected to two rounds of sequencing and the remaining nine pairs to a single round. Both rounds of sequencing for the first six pairs utilized existing libraries created during the initial sequencing of the 96 tumor/normal pairs. In the first round of sequencing, one library pool was created for capture (total library yield into the hybridization was 2.5 µg and included all 12 libraries) and was sequenced on one lane of HiSeq2500 (2×125 reads). Similarly, for the second round, one library pool was created for capture (total library yield into the hybridization was 4.8 µg and included all 12 libraries) and was sequenced on the Rapid Run mode on the HiSeq2500 (two lanes on one flow cell generating 2×100 reads).

Deep sequencing of the final nine sample pairs was performed by first constructing automated dual indexed libraries with 250 ng of genomic DNA utilizing the KAPA® HTP Library Kit (KAPA Biosystems, Wilmington, Mass.) on the SCICLONE® NGS instrument (Perkin Elmer, Waltham, Mass.) targeting 250 bp inserts. Four independent 3 µg library pools were created from nine cases including both tumor/normal libraries. Each library pool was hybridized with the custom biotinylated Nimblegen probe set in solution. The concentration of each captured library pool was accurately determined through qPCR according to the manufacturer's protocol (KAPA Biosystems) to produce cluster counts appropriate for the ILLUMINA® HISEQ® 2500 IT (Illumina, Inc., San Deigo, Calif.) platform (2×125 reads).

Sequencing Coverage Calculation

Average depth and on-target efficiency were calculated using the Genome Modeling System's (Griffith, M., PLoS Comput. Biol., 2015, 11, e1004274) utilities for measuring depth and alignment coverage. These tools rely on the RefCov software suite (gmt.genome.wustl.edu), which provides a number of methods for analyzing nucleotide sequence coverage. RefCov calculates summary and per-base position coverage statistics relative to a reference genome based on an input alignment BAM file. Reported mean, minimum, and maximum coverage statistics are based on on-target bases—i.e., bases aligned within the coordinates of the designed probes, as specified by the BED file (Table 1). Hence, no bases within the wingspan of the probes were considered on-target. Per-base coverage was then calculated for each base in the target space. A sample's mean coverage was then calculated as the mean per-base coverage across all bases having at least 1× coverage. The reported mean, minimum, and maximum coverages are then the mean, minimum, and maximum across all samples of the per-sample mean coverages. Finally, percent on target efficiency at a specified depth (30×) was calculated by first summing the total coverage at on-target bases that meet or exceed the specified depth and then by dividing this sum by the total number of bases sequenced.

Capture Sequencing-Based Copy Number Detection

Copy number variants (CNVs) were called using Copy-CAT2 (Sehn, J. K., et al., Exp. Mol. Pathol., 2014, 97, 69-73) parameterized to detect copy number alterations exceeding the level of noise estimated from diploid regions using a gaussian mixture model. CopyCAT2 was specifically developed to detect CNVs from capture sequencing data. CNVs were called if the (nominal) binomial p-value output by CopyCAT2 (p.cov.np) was less than 0.05, which is computed based on the number of capture probes having a tumor/normal depth log ratio outside some upper or lower limit. These upper and lower limits were defined as the mean plus or minus, respectively, two times the standard deviation of the distribution of log ratios from a "typical" diploid region. Chromosome 2 was generally used as the reference diploid region, as it is infrequently altered in multiple myeloma. In several instances, however, chromosome 2 proved too noisy and a different chromosome was used as the diploid region, namely: chromosome 10 for samples H_QD—WAPAT023-V0DHO9, H_QD-WAPAT025-V0DHOD, H_QD-WAPAT030-V0DHON, and H_QD-WAPAT032-V0DHOR and chromosome 17 for samples H_QD-WAPAT082-V0DHRJ, H_QD-WAPAT052-V0DHPV, H_QD-WAPAT056-V0DHQ3, and H_QD-WAPAT014-V0DHNR. Additionally, two samples were excluded from copy number analysis: H_QD-WUPAT001-V0DHMT had low coverage and H_QD-WUPAT002-V0DHMW showed poor correlation between tumor and normal.

To prevent the upper and lower limits from being overly sensitive to potential focal and/or arm-level CNVs within the supposedly diploid region, a gaussian mixture model (i.e., sum of gaussian distributions) was fit to the tumor/normal ratios (not their log-transformed values) within the region. Since the bulk of the region was assumed diploid, the gaussian making the largest contribution to the mixture (i.e., with the largest weight and hence representing the most probes) was taken as a model of the unaltered subregions. The gaussian mixture model was fit using a variational Bayesian approach implemented in the R bmm package and used previously as the backend of SciClone—a method for inferring clonal evolution from sequencing data (Miller, C. A., et al., PLoS Comput. Biol., 2014, 10, e1003665). The mixture was fit with two gaussian components by: invoking init.gaussian.bmm.hyperparameters with N.c=2, passing the resulting initialized hyperparameters to init.gaussian.bmm.parameters, and finally passing the parameters resulting from that call, along with the hyperparameters, to gaussian.bmm. gaussian.bmm was also passed parameters convergence.threshold=$10^{-4}$, max.iterations=10000, and pi.threshold=$10^{-2}$. The data passed to these functions were output by an initial call of CopyCAT2. CopyCAT2 was invoked independently for each tumor sample, with the corresponding normal sample used as the (single) control sample, and with parameters coverage.min.ratio=0.125, coverage.max.ratio=8, min.num.normals=1, min.norma.corr=0.5, segalpha=0.05, and vafs_normalize=FALSE. Additionally, the BED file describing the custom capture probes (Table 1) was passed as the target.bedfile parameter after first excluding IGH coordinates. This effectively prevents CopyCAT2 from attempting to call CNVs within the IGH locus. This BED file was used to calculate coverage using bedtools coverage, which was subsequently passed to CopyCAT2.

Following fitting of the gaussian mixture, CopyCAT2 was invoked a second and final time to detect CNVs based on the margins established by the fit. Parameters were as specified above in the initial run, except with coverage.min.ratio and coverage.max.ratio set to the mean (which is one, since CopyCAT2 mean centers the data) plus or minus twice the standard deviation of gaussian model of the unaltered regions.

CNVs output by CopyCAT2 were annotated to indicate whether they were amplifications (CopyCAT2 finalcn field >2) or deletions (finalcn <2), whether they were focal or arm-level, whether they participated in a hyperdiploid event, and, for focal CNVs, what genes they encompassed. A CNV was annotated as belonging to a chromosome arm if at least one breakpoint was within that arm; it was labeled as "arm"-level if its length was at least half the length of the targeted region of the arm and "focal" otherwise (Table 2). An event that involved both arms of the chromosome was annotated for both the p- and q-arms, with a separate entry in the table (Table 2) for each. A sample was considered hyperdiploid if it had amplifications of at least five of the chromosomes 3, 5, 7, 9, 11, 15, 19, and 21 (i.e., both p- and q-arms, except for chromosome 15, since 15p was not targeted). Focal CNVs were annotated with (hg19) genes they encompassed using findOverlaps from the GenomicRanges R package.

Capture Sequencing-Based Translocation Detection

Translocations were detected using LUMPY (Layer, R. M., et al., Genome Biol., 2014, 15, R84), with results filtered by a machine learning approach optimized to achieve high precision relative to available FISH results. First, FASTQ files were aligned against the human genome (hg19) using the aln command of SpeedSeq5 (v0.0.1) and parameters "-t 4 -o prefix," which resulted in three BAM files: prefix.bam containing all alignments, prefix.splitters.bam containing all split reads, and prefix.discordants.bam containing discordant read pairs. The empirical insert size distribution was calculated for each alignment BAM file using the pairend_distro.py utility distributed with LUMPY (Layer, R. M., et al., Genome Biology, 2014, 15, R84). Specifically, samtools6 was used to output the entries of the prefix.bam file, with the first 10,000 entries skipped and the remainder piped to pairend_distro.py with parameters "-X 4 -N 10000," with results output to prefix.hist. The mean m and standard deviation sd of the insert size for prefix.bam were parsed from prefix.hist and used to define back_dist=m+3*sd. LUMPY (v0.2.13) was then invoked independently for each patient, with paired-end "pe" and split read "sr" arguments for each discordant and split-read BAM file (for both tumor and normal samples), respectively, associated with that patient. Specifically, each prefix.bam file associated with the patient resulted in a set of arguments: "-pe id:<sample_name>, bam_file:prefix.discordants.bam, histo_file:prefix.hist, mean:m,stdev:s d,read_length: <read_length>,min_non_overlap:<read_length>,discordant_z:5,back_distance:bac k_dist, weight:1,min_mapping_threshold:<threshold>" and "-sr id:<sample_name>,bam_file:prefix.splitters.bam, back_distance: back_dist,weight:1,min_mapping_threshold:<threshold>," where <sample_name> was the name of the sample, <threshold> was 50, and <read_length> was the mode of the lengths of the first 110,000 reads (as determined by outputting the first 110,000 reads of prefix.bam using samtools), which was 100. Translocations were annotated with the nearest cancer—associated gene (as cataloged in the cancer gene census7) within 1 Mb of either breakpoint.

Putative translocations involving IGH (defined as those with a partner within the region chr14:105982614-107338051) or MYC (chr8:128697680-128853674) were parsed out of the LUMPY VCF (variant call format) output using a custom script. In addition to the indicated coordinates, putative translocations were required to include a VCF MATEID field and SVTYPE=BND (indicating a complex rearrangement with two breakends).

Each putative inter-chromosomal IGH translocation was further filtered using a support vector machine (SVM)

trained on available FISH data and using as input the number of split reads (indicated by the SR=<num_reads> field of the LUMPY VCF output file) and the number of paired-end reads (indicated by PE=<num_reads>) supporting the translocation. The SVM was trained to perform binary discrimination between putative IGH translocation calls that were and were not validated by FISH. Only those LUMPY inter-chromosomal IGH translocation calls involving (non-MYC) canonical partners were used during the SVM training and test phases—i.e., those with one breakpoint on chromosome 14 within the region spanning from 1 MB up- to 1 MB down-stream of IGH (chr14:105982614-107338051) and with a second breakpoint on one of the canonical IGH partner chromosomes, spanning from 1 MB up- to 1 MB down-stream of genes previously implicated in IGH translocations (Walker, B. A., et al., Blood, 2013, 121, 3413-3419) on chromosomes 4 (near genes FGFR3, LETM1, or WHSC1), 6 (CCND3 or UBR2), 11 (PPP6R3, TPCN2, MYEOV, or CCND1), 16 (WWOX or MAF), or 20 (DHX36, LOC339568, or MAFB). A LUMPY call of a canonical IGH translocation was considered validated by FISH if the corresponding partner was detected in a tumor sample at the Mayo Clinic and/or the sample collection site. In no case did FISH performed at the Mayo Clinic and the sample collection site detect different IGH translocations. A LUMPY call of an IGH translocation was not considered validated by FISH if it was called within one of the paired normal samples (which were assumed not to harbor translocations) or if it disagreed with the translocation inferred by either site. The requirement that LUMPY and FISH not disagree effectively implies the assumption that a patient sample not harbor multiple IGH translocations—with the exception of a secondary t(8;14) translocation, which was not considered during SVM training.

Tuning of a linear SVM was performed with five-fold cross-validation in Python using the scikit-learn library. Specifically, LUMPY calls of canonical IGH translocations in tumor samples subjected to FISH assay or in the corresponding normal samples were partitioned into equally-sized training and test sets, stratified by whether they were or were not validated by FISH using train_test_split with the stratify parameter. At most one LUMPY call involving each partner chromosome was considered during the training and test phase—if LUMPY inferred multiple calls involving the same partner, only that call with the largest total evidence (number of supporting split reads plus number of supporting paired reads) was considered. LUMPY calls in normal samples were, by assumption, not considered validated by FISH. The C parameter of the linear SVM was tuned on the training data via a grid search over the values C:={$10^{-4}$, $10^{-3}$, $10^{-2}$, $10^{-1}$, 1, 10, $10^2$, $10^3$, $10^4$}} and using five-fold cross-validation with GridSearchCV(SVM(kernel='linear', C=1), [{'C': 10**x for x in range(-4,4)}], cv=5, scoring='precision_micro'). The best fit was obtained with C=0.1, which was subsequently applied to the held-out test samples to evaluate precision and recall and to call IGH translocations across all samples, including those involving MYC and non-canonical partners, t(8;14) translocations were those LUMPY calls that passed the SVM filter and that had a breakpoint within 1 MB up- or down-stream of MYC.

FISH results for MYC translocations were not available for filtering LUMPY results. Hence, the inventors manually defined a decision boundary in the space of number of supporting split reads and paired-end reads to separate those LUMPY calls that were likely to be false positives (in particular, those that were detected in normal samples) from those more likely to be true positives. To do so, independently for intra- and inter-chromosomal MYC translocations, the inventors defined the separating hyperplane such that all translocations inferred in normal samples were assigned to the likely false positive class. Specifically, they manually selected translocations based on their numbers of supporting reads that should be used to define the boundary (i.e., a subset of which would be selected as support vectors to define the hyperplane). This was accomplished by defining an SVM via SVM(kernel='linear', C=1) and then by invoking its fit method with a sample_weight argument that assigned a non-zero weight (10) to the manually-selected translocations and zero weight to all others. In the case of intrachromosomal translocations, the manually selected false positive translocation was at (number of split reads=2, number of paired-end reads=2) and the true positive translocations were at (7, 6) and (0, 7). Note that the plotted numbers of supporting reads have been jittered so that overlapping translocations are visible. In the case of inter-chromosomal translocations, the manually selected false positive translocation was at (8, 8) and the true positive translocation was at (28, 39). This approach ensured that we could identify putative (but presumably false positive) MYC translocations in normal samples with 100% precision based on number of supporting split and paired-end reads. The inventors subsequently filtered any MYC translocations in tumor samples that were assigned by the SVM to the same class as the normal sample translocations.

Mapping of IGH Constant, Switch, and Enhancer Regions

The following genes were searched on Ensembl GRCh37: IGHA2, IGHE, IGHG4, IGHGP, IGHA1, IGHEP1, IGHG1, IGHG3, IGHD, IGHM and the "Location" of each gene served as the IGH constant regions. The inventors identified switch regions as those regions enriched for repeats downstream of the constant regions. To do so, they entered the coordinates of the constant regions above into the UCSC Genome Browser (genome.ucsc.edu) with the following parameters: a. Group: Mammal b. Genome: Human and c. Assembly: February 2009 (GRCh37hg19). Dropdown controls were used to hide everything except:

a. Mapping and Sequencing >Base position >Full
b. Genes and Gene Prediction >USCS Genes >Full
c. Genes and Gene Predictions >Ensembl Genes >Full
d. Genes and Gene Predictions >Vega Genes >Full
e. Repeats >Simple Repeats >Full This displays simple tandem repeats located by Tandem Repeats Finder. Repeat regions located downstream of the constant region were treated as the switch regions for the adjacent constant region. Some of the switch regions were separated into non-contiguous tandem repeats with repeating sequences, so the whole region spanning these repeats was treated as the switch region. To confirm the validity of this approach, the inventors used BLAT to map the known (Sun, Z. J. & Kitchingman, G. R., DNA Seq 1, 1991, 347-355) sequence (GenBank: X54713.1) for the mu switch region to the hg19 coordinates chr14:106322327-106326797. This corresponds closely to those that were inferred using the above tandem repeat-based method (chr14:106323230—106326599).

The 3' enhancer region coordinates were determined by using BLAT to map the reported (Mills, F. C., et al., J. Exp. Med., 1997, 186, 845-858) enhancer elements. The range of the four sequences downstream of IGHA1 (GenBank: AF013718.1, AF013722.1, AF013722.1, AF013725.1) was determined to be chr14:106152458-106167601 (hg19 coordinates) and used to define the "E3A1" enhancer. Similarly, the three sequences downstream of IGHA2 (AF013719.1, AF013724.3, AF013726.1) mapped to a range chr14:

106032614—106048676 that we used to define the "E3A2" enhancer. The mu enhancer region coordinates were determined by using BLAT to map the sequence TTTTTTAAT-TAATTGAGCGAAGCTGGAAGCAGATGATGAATT-AGAGTCAAGA
TGGCTOCATGGGGGTCTCCGGCACC-
CACAGCAGGTGGCAGGAAGCAGGTCA
CCGCGAGAGTCTATITAG-
GAAGCAAAAAAACACAATTGGTAAATTTATCAC
TCTGGTTGTGAAGAGGTGGTIIIGCCCAGCCCA-
GATCTGAAAGTGCTCTACT
GAGCAAAACAACACCTGGACAAT-
TTGCGTTCTAAAATAAGGCGAGGCTGA
CCGAAACTGAAAAGGCTTTTTTTAACTATCTGAAT-
TTCATTTCCAAT CTTAGCTTA (SEQ ID NO: 1) reported in FIG. 5 of Hayday, A. C., et al. (Nature, 1984, 307, 334-340).

Validation of Novel t(14,22) Translocation

Polymerase chain reaction (PCR) was performed on two nanograms of genomic DNA isolated from CD138+ selected bone marrow (tumor) biopsy and peripheral blood leukocytes (germline) from the patient that was called positive for the t(14;22) translocation by capture sequencing. Primers were designed to span the translocation breakpoints on the derivative chromosomes based on the base-pair resolution reads from capture sequencing. Reactions were run using GoTaqGreen Master Mix (Promega) per manufacturer's instructions with oligos designed to detect derivative chromosome 14 [Forward: ACCACTAACAGGGGACATGC (SEQ ID NO: 2) and Reverse: TTTGATTATTCCCC-CAACCA (SEQ ID NO: 3)] and derivative chromosome 22 [Forward: ACAAGCCAGAGGAGTGAGGA (SEQ ID NO: 4) and Reverse: CTCTGAAGACCAGGCTCACC (SEQ ID NO: 5)]. PCR products were separated with DNA electrophoresis; products specific to tumor samples and of the expected size were cut out and DNA was isolated using the ZYMOCLEAN™ (Zymo Research, Irvine, Calif.) Gel DNA Recovery Kit (Genesee Scientific) per manufacturer's instructions and sequenced using the same primers as the PCR reactions. The sequences were mapped to the human genome (GRCh37 assembly) using BLAT (UCSC genome browser) and alignments with genomic locations matching breakpoints obtained from capture sequencing were identified to confirm the presence of t(14;22) translocation in the gDNA.

The quality of DNA was checked by detecting the presence of chromosomes 14 and 22 wild-type for the translocation in the same DNA samples mentioned above. For the translocation, two breakpoints were present on each chromosome and the region between the breakpoints was deleted from the translocated chromosomes. Oligos were designed that spanned the deleted section of chromosomes 14 [Forward: GGGCTGTTCTCTGTGGTAT (SEQ ID NO: 6) and Reverse: GTGGAATGTGTGTGAGCTGG (SEQ ID NO: 7)] and 22 [Forward: ATAGGGTCCGTGCACCATTC (SEQ ID NO: 8) and Reverse: ATGCTGAGCTAAC-CACCCTT (SEQ ID NO: 9)], and PCR products were analyzed by agarose gel electrophoresis.

Validation of Novel t(13;14) Translocation

Polymerase chain reaction (PCR) was performed on two nanograms of genomic DNA isolated from CD138+ selected bone marrow (tumor) biopsy and peripheral blood leukocytes (germline) from the patient that was called positive for the t(13;14) translocation by capture sequencing. Primers were designed to span the translocation breakpoints on the derivative chromosomes based on the base-pair resolution reads from capture sequencing. Reactions were run using GOTAQ® Green Master Mix (Promega, Madison, Wis.) per manufacturer's instructions with oligos designed to detect derivative chromosome 13 [Forward: AATCTTTCTGTTCTGTTGGCATT (SEQ ID NO: 10) and Reverse: CTGGACTGATCTGGGCTAGG (SEQ ID NO: 11)]. PCR products were separated electrophoretically; products specific to tumor samples and of the expected size were cut out and DNA was isolated using the ZYMO-CLEAN™ (Zymo Research, Irvine, Calif.) Gel DNA Recovery Kit (Genesee Scientific) per manufacturer's instructions and sequenced using the same primers as the PCR reactions. The sequences were mapped to the human genome (GRCh37 assembly) using BLAT (UCSC genome browser) and alignments with genomic locations matching breakpoints obtained from capture sequencing were identified to confirm the presence of t(13;14) translocation in the gDNA.

Somatic Single Nucleotide Variant Detection

Reads were aligned against human reference genome GRCh37-lite using BWA (Li, H. & Durbin, R., Bioinformatics, 2009, 25, 1754-1760). The SNV-calling pipeline used a combination of samtools (Li, H. et al., Bioinformatics, 2009, 25, 2078-2079), SomaticSniper v. 1.0.4 (Larson, D. E., et al., Bioinformatics, 2012, 28, 311-317), MuTect 1.1.4 (Cibulskis, K., et al., Nat. Biotechnol., 2013, 31, 213-219), Strelka v. 1.0.11 (Saunders, C. T., et al., Bioinformatics, 2012, 28, 1811-1817), and VarScan version 2.3.6 (Koboldt, D. C., et al., Genome Res, 2012, 22, 568-576). To obtain a final set of calls, the somatic variation detection pipeline executes a series of union and intersection mergers to integrate the results of these tools.

First, SNVs are called using SAMtools version r982 (parameters: mpileup-BuDS) filtered by snp-filter version v1 and false-positive-filter v1 (parameters: -max-mm-qualsum-diff 100—bam-readcount-version 0.4—bam-readcount-min-base-quality 15) and intersected with Somatic Sniper version 1.0.4 (parameters: -F vcf-G -L -q 1 -Q 15) filtered by false-positive v1 (parameters: —bam-readcount-version 0.4—bam-readcount-min-base-quality 15) then somatic-score-mapping-quality v1 (parameters: —min-mapping-quality 40—min-somatic-score 40). A union join of these results is then performed with the output of the following 3 callers: (1) VarScan 2.3.6 (parameters: —nobaq —version r982) filtered by varscan-high-confidence v then false-positive v1 (parameters: —bam-readcount-version 0.4—bam-readcount-min-base-quality 15); (2) Strelka version 1.0.11 (parameters: isSkipDepthFilters=1); (3) MuTect 1.1.4 (parameters: —number-of-chunks 50; —cosmic-vcf b 37_cosmic_v54_120711.vcf —dbsnp-vcf snvs.hq.vcf). The b37_cosmic_v54_120711.vcf represents the 1000-genomes format of the variants contained within COSMIC, while snvs.hq.vcf contains known the dbSNP variants from human build 142.

In addition to producing the standard position and base pair change of a variant, the somatic variation pipeline produces both a classification for mutation type (e.g., silent, missense, nonsense) as well the reference and alternate read counts and variant allele frequencies for both the tumor and matched normal samples. Together, this information provided a means of stratifying variants by relative importance and of assessing the sensitivity of the custom capture platform to detect low-frequency mutations.

Comparison Between Initial Capture and Subsequent Deep Sequencing

The inventors explored the sensitivity afforded by increased sequencing depth by performing additional sequencing of 15 tumor (mean depth=1,259×, min=506×, max=1,660×) and paired normal (mean=1,326×, min=763×, max=1,727×) samples. They then performed a comparison of variants discovered by the initial and deeper sequencing. Both data sets were processed using the same pipeline parameters as detailed above. The final SNV variant calls were then compared to look for commonalities as well as those unique to each set.

Several filtering steps were carried out prior to the comparison of variants. This served to both highlight the genes of interest, as well as to account for the additional information provided by deeper sequencing. This additional information influences SNV results both by revealing rare low-frequency variants as well as by identifying potential contamination in the original lower-coverage results. For instance, a SNV with low variant allele coverage in the initial sequencing may be called if reference coverage is also low, so that the resulting VAF is appreciable and exceeds the caller's threshold. However, if deeper sequencing leads to additional coverage of that reference allele, without a corresponding increase in the variant allele, the resulting VAF may fall below a caller-required threshold and be filtered. This situation may indicate the variant reads are artifacts.

The following variants were removed prior to comparison between initial and subsequent deep sequencing:
1. Those annotated as intronic, intergenic, silent, or 5' flanking (to focus the comparison on those variants most likely of biological importance).
2. Those occurring in the IGH region (as these are likely caused by physiological somatic hypermutation and are not of biological significance).
3. Those rejected by a caller as likely germline in either data set.

Sequencing Downsampling

The inventors explored the effect of varying read depth on variant discovery by downsampling the deep sequencing data sets. Comparisons were performed at 25%, 50%, and 75% of the total coverage on the set of 15 samples for which additional sequencing was performed. The original BAM files containing all instrument data were first query-sorted using the SortSam utility from the Picard 1.138 toolkit (parameters: SORT_ORDER=queryname VALIDATION_STRINGENCY=LENIENT). To recreate the effects of lower coverage, the query-sorted instrument data were then randomly down-sampled without replacement using the barn-sample tool from the fastq-tools package (version 0.8). Five repetitions of subsampling were performed on the 15 samples at all three levels of lower coverage. The reduced data sets were then imported into the standard somatic variation pipeline (above) to maintain consistency with the samples having full coverage. SNV calls from the downsampled results were excluded from the comparison as above or if they were annotated as RNA mutations. After filtering, the results were compared to the full complement of calls from the 100% coverage data set.

Comparison Between Exome and Capture Sequencing

In order to establish performance against an existing platform, the inventors compared the results of capture sequencing to those previously obtained via exome sequencing (dbGaP Study Accession: phs000348.v2.p1). The inventors downloaded alignment BAM files from dbGaP, converted them to FASTQ files, and reprocessed the unaligned reads using the same alignment and variant discovery pipeline as used for the capture sequencing data (supra). This ensured that discrepancies reported between the two studies were not an artifact of different bioinformatic pipelines, but rather reflected differences in the sequencing platforms employed. Though 79 pairs overlapped between the two studies, they were only able to reprocess the data from 44 pairs, which are reported here.

To address the issue of the capture platform's much more restricted coverage, the comparison was limited to only those coordinates nominally targeted by the probes (Table 1). To further equalize the comparison, the inventors extended the specification to include only those regions in the exome and capture that possessed a baseline level of 10× coverage in at least 50% of the samples. Namely, a position was required to have at least a minimum of ten reads supporting it in both the normal as well as the tumor samples, in at least half of the capture and half of the exome results. This provided a set of positions between both platforms where affinity is consistent. The bedtools (version 2.17.0) utility multicov was used to extract the read counts from both tumor and normal samples from the exome and capture-based sequencing alignments.

Enrichment for c-AID Signature Amongst IGLL5 Mutations

Five of 40 IGLL5 variants (in 25 patients) were consistent with a c-AID signature [i.e., mutation of C to T or G at a WRCY motif, where W=A or T, R=purine (G or A) and Y=pyrimidine (C or T)]. The inventors determined the likelihood that this number of c-AID-induced mutations would occur by chance using a binomial test, where the binomial probability was the background probability of such a mutation within the gene. They empirically estimated this probability to be 0.005 by defining it as the product of the following probabilities: (1) the probability (observed frequency within the data) that a four-nucleotide motif within the sequenced region of IGLL5 is a WRCY (19/632); (2) the probability of mutating the C (not the Y) within this motif (1/4); and (3) the probability (observed frequency within the data) of a C being mutated to either a G or a T (8/11).

Mutual Co-Occurrence and Mutual Exclusivity

Mutation co-occurrence and mutual exclusivity were calculated using MuSiC.17 Raw p-values calculated using 100,000 permutations are reported.

IGLL5 Survival Analysis

Clinical and non-synonymous SNV and indel data were downloaded from the MMRF Researcher Gateway as part of CoMMpass trial IA9 data release (files STAND_ALONE_SURVIVAL.csv and MMRF_CoMMpass_IA9_All_Canonical_NS_Variants.txt). These data were generated as part of the Multiple Myeloma Research Foundation Personalized Medicine Initiatives (research.themmrf.org and www.themmrf.org). Progression events and times were defined using the "ttcpfs" and "censpfs" fields, respectively, from the file STAND_ALONE_SURVIVAL.csv. Survival analysis was performed in R using the survival and survminer packages: Kaplan-Meier curves were generated using survfit and plotted using ggsurvplot, while a Cox proportional hazards model was fit using coxph.

Fluorescence In Situ Hybridization

Fluorescent in situ hybridization (FISH) was performed on ACK lysed BM aspirates using cIg-FISH as previously described (Ahmann, G. J., et al, Cancer genetics and cytogenetics, 1998, 101, 7-11). All samples were hybridized with commercial probes (Abbott/Vysis). A dual color break apart probeset for 14q32 was first used to determine if there was a translocation involving the IGH locus. If the break apart was positive, a reflex to the most common translocations observed in multiple myeloma were used: t(11;14)(q13;q32) (i.e., CCND1/IGH), followed by t(4;14)(p16.3;q32) (i.e., FGFR3/IGH), and then lastly t(14;16)(q32;q23) (i.e., IGH/MAF).

RNA-Seq Expression Data

RNA-seq expression data from MM samples were obtained from the Multiple Myeloma Research Foundation (MMRF) Researcher Gateway (rna_expr.eligible.gct; research.themmrf.org). A gene was considered expressed in MM and hence eligible for inclusion on the targeted capture panel if its expression exceeded an FPKM of 0.001 in at least half of the 33 samples in the data set. DERL3 expression across MM samples was obtained from the interim analysis 7 (IA7) release of the CoMMpass trial, which was also downloaded from the MMRF Research Gateway.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates the design of an oligonucleotide probe array for targeted sequence capture.

The present inventors developed a multiple myeloma (MM)-specific custom capture sequencing platform capable of detecting CNVs, SNVs, and translocations. They designed oligonucleotide probes covering 3.3 Mb of genomic space and complementary to the exons, untranslated regions, and splice sites of 465 genes (Tables 1 and 3) which are expressed in MM and that: (1) are annotated as cancer genes (in COSMIC (Forbes, S. A., et al., Nucleic Acids Res., 2015, 43, D805-811) or MutSig (Lawrence, M. S., et al., Nature, 2013, 499, 214-218)), (2) function in DNA repair or B cell biology, (3) are mutated at a frequency of >3% in published studies (Bolli, N., et al., Nat Commun., 2014, 5, 2997; Chapman, M. A., et al., Nature, 2011, 471, 467-472), or (4) have mutations that cluster in hotspots. To detect IGH translocations, the present inventors also designed probes tiled in an unbiased fashion across the locus, including within the variable (IGHV), diversity (IGHD), joining (IGHJ), and constant/switch regions. The inventors also designed probes targeting the exonic regions of canonical IGH translocation partners (CCND1, CCND3, FGFR3, MAF, MAFB, WHSC1, and WWOX). To capture secondary MYC translocations, probes were tiled across exonic and intronic regions of the MYC locus.

Example 2

This example illustrates the sequencing of 95 paired tumor cell and normal cell DNA samples.

The present inventors used the platform to sequence DNA isolated from 95 tumor (CD138-purified cells isolated from bone marrow aspirates) and paired normal (blood) samples. The per-sample average probe depth averaged across all tumor samples was 496× (min=211×, max=701×) and across all normal samples was 547× (min=226×, max=863×). These samples were specifically selected to validate the platform and to tune the computational methods as a subset of them were previously subjected to exome sequencing (44 samples) and/or FISH (22 samples) analysis of IGH translocations. The present experiments achieved a mean sequencing depth of 104× (min=33×, max=140×; across the tumor samples and of 107×124 (min=43×, max=168×) across the normal samples.

Example 3

This example illustrates targeted capture sequencing identifies copy number alterations with prognostic significance.

Figure 2:
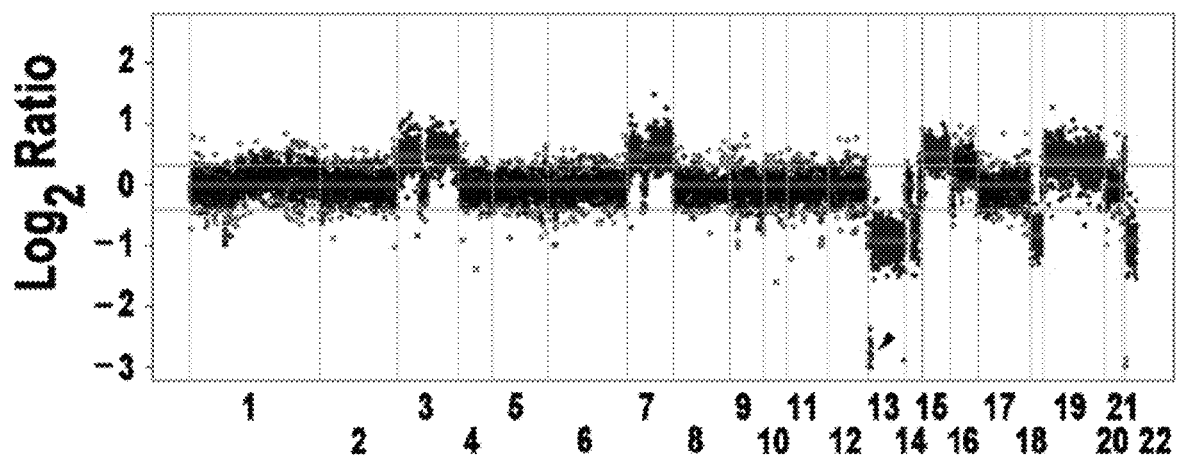
FIG. 2 illustrates identification by targeted sequencing of chromosome-level, arm-level, and focal CNVs in focal copy number events (arrow) detected by CopyCat2 (blue; $p<0.05$) from $\log_2$ ratios of tumor to paired normal sequencing depth (y axis) across chromosomes (x axis).

The broad coverage of the platform [across chromosome arms (Table 4) and 465 genes] facilitated detection of chromosome-level, arm-level, and focal CNVs. The inventors identified these events computationally from the per-probe ratios of tumor to normal sequencing depth using CopyCAT2 (Sehn, J. K., et al., Exp. Mol. Pathol., 2014, 97, 69-73). To reduce false positives, the inventors developed an approach that filtered CNV calls with ratios below a noise level estimated from diploid regions. All tumor samples harbored at least one somatic (missense, nonsense, or frame shift) mutation, with each sample having an average of 20 mutations (FIG. 1-2). Ninety-four of 95 tumor samples had a mutation predicted to be deleterious by Poly-Phen2 (Adzhubei, I. A., et al., Nat. Methods, 2010, 7(4), 248-249) or SIFT (Kumar, P., et al., Nat. Protoc., 2009, 4(7), 1073-1081), with each sample having an average of twelve deleterious mutations (FIG. 1-2). Eighty-six samples had multiple mutations in a single gene. These multi-hit genes included ATM, BRCA2, CARD11, CCND1, CCND3, CYLD, DIS3, DNAH5, DNAH11, DNMT3A, FAM46C, FGFR3, JAK2, KDM6A, KDM6B, KIT, KRAS, MAF, MAFB, MTOR, MYC, NFKB1, NOTCH1, NOTCH2, PARP1, RB1, TRAF3, and WHSC1. Of the mutations in these genes, some of them can be confirmed to be bi-allelic (i.e., on independent sequencing reads as viewed in IGV). In cases with bi-allelic mutation, one of the mutations was subclonal [variant allele frequency (VAF)<30%] in a percentage of cases. Other genes exhibiting cosmic-overlap mutations with multiple hits include CLIP1, CSMD3, EP400, FMN1, FRG1B, KDM6A, KRAS, LAMA1, MLLT3, MSH2, MSH6, NOTCH1, OR1S2, PAX5, and RB1.

In addition, in the instant data set, IGLL5 was the third highest mutated gene, and involved in the t(14;22) translocation detected by the present array. However, IGLL5 may be underrepresented in other sequencing arrays since, due to its genetic location, it may have been excluded from the platform. The inventors' approach also identified the full range of CNVs, from genome-scale hyperdiploid events (FIG. 1; Table 4) to focal events, including a homozygous deletion that encompassed BRCA2 (FIG. 2). FIG. 1 and FIG. 2 show hyperdiploid and focal copy number events detected by CopyCat2 (blue; p<0.05) from $\log_2$ ratios of tumor to paired normal sequencing depth across chromosomes. Red lines indicate segments; green lines indicate margins outside of which segments are considered altered. (Clonal) single-copy gains occur at a $\log_2$ ratio of $\log_2(3/2)$ ~0.58, whereas (clonal) heterozygous/single-copy losses occur at a $\log_2$ ratio of $\log_2(1/2)=-1$. Homozygous losses occur, in principle, at $\log_2(0/2)$ or negative infinity. The finite negative ratio of the homozygous focal loss (FIG. 2) may indicate that it is subclonal and/or reflect a small number of spurious alignments to this region of the genome. Detected arm-level events included those associated with poor prognosis, such as amp(1q), del(1p), del(13q), and del(17p) (reviewed in Griffith, M., et al., PLoS Comput. Biol., 2015, 11, e1004274).

Example 4

This example illustrates that targeted capture sequencing identifies IGH translocations.

Figure 3:
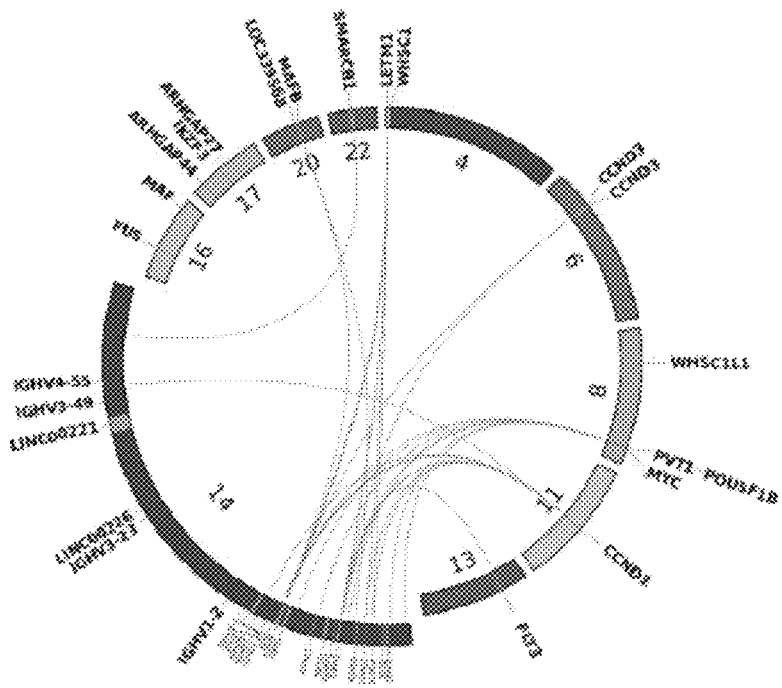
FIG. 3 illustrates a Circos plot of IGH translocations in which chromosomes involved in translocations are magnified to highlight regions and genes near breakpoints.
Figure 4:
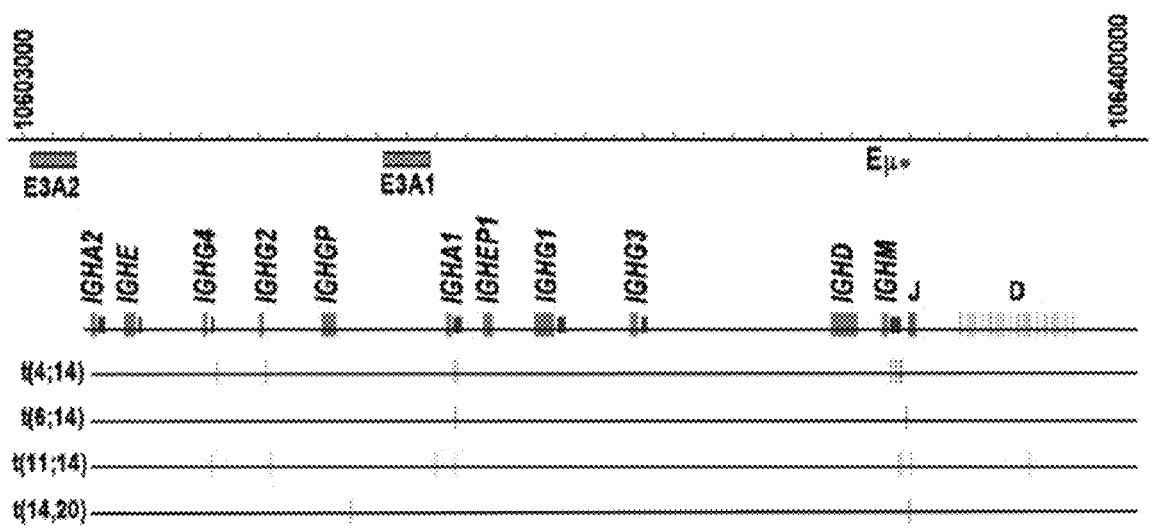
FIG. 4 illustrates breakpoints (vertical lines) of canonical IGH translocations within IGH locus.

The inventors detected IGH translocations using LUMPY and again developed a filtering strategy to reduce likely false positives. They filtered putative translocations based on thresholds on the number of supporting split reads and discordant paired-end reads. They tuned the thresholds to maximize precision using a machine learning approach involving a support vector machine (SVM) and available FISH data, resulting in a precision of 100% and a recall of 64%. Canonical IGH translocations were then detected by the platform near expected frequencies (Table 5; FIG. 3) and occurred predominantly within the IGH constant region, but also telomeric of the IGHM switch region and occasionally within the D and J regions (FIG. 4). In FIG. 4, E3A2 and E3A1 represent 3' enhancer elements downstream of IGHA2 and IGHA1 genes, respectively. EMU represents a mu enhancer. The purple boxes denote switch regions. FIG. 4 is to scale. Notably, one of the t(11;14) translocations occurred within the constant region, but outside all constant and switch segments. No translocations within the V region passed the filtering step.

In addition, a complex translocation affecting chromosomes 14, 13, and 11 was also detected. The breakpoint on chromosome 13 was nearby FLT3. PCR analysis was used to confirm that a chromosome 13 location was translocated to IgH on chromosome 14. Together, the array efficiently detected known translocation, and also identified two novel translocations.

Example 5

This example illustrates that IGLL5 is translocated and co-incident with over-expression of DERL3 in multiple myeloma.

To prioritize novel IGH translocations as potential driver mutations, the inventors identified cancer-associated genes within 1 Mb of each chromosomal breakpoint (Table 6). The two annotated translocations with largest total evidence (sum of number of supporting split reads and number of discordant paired-end reads) were analyzed further. The first was a complex translocation involving chromosomes 11, 13, and 14. The putative breakpoint on chromosome 13 was nearby FLT3 (<0.5 Mb); the inventors validated that chromosome 13q12.2 was indeed translocated to IGH on chromosome 14 using PCR.

Figure 5:
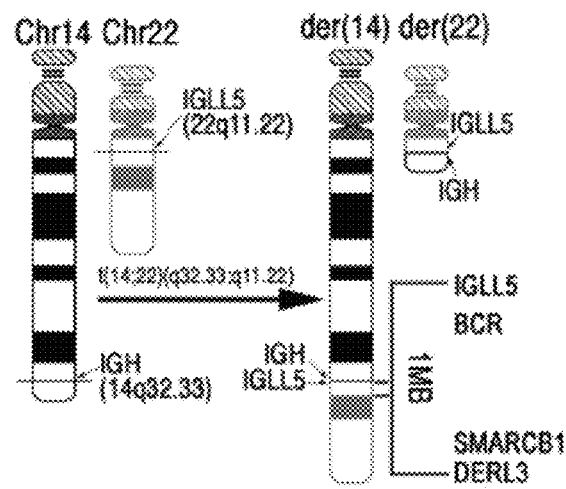
FIG. 5 illustrates a schematic of validated t(14;22) translocation. (Left) Normal chromosomes 14 and 22 with horizontal lines indicating location of breakpoints within the IGH and IGLL5 loci, respectively. (Right) Two derivative (der) chromosomes, each retaining a portion of its respective IGH or IGLL5 gene.
Figure 6:
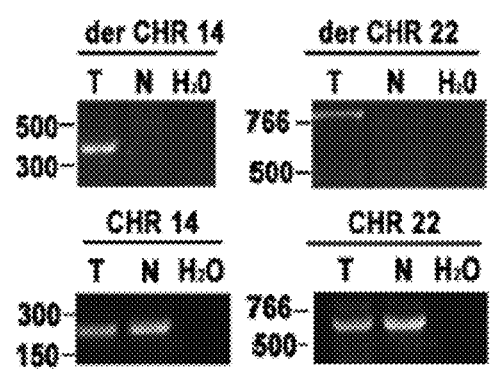
FIG. 6 illustrates PCR validation of t(14,22) translocation. Oligos specific to each breakpoint used in PCR reactions (top). Oligos specific to the small regions deleted on der(14) and der(22) were designed to detect non-translocated allele (bottom).

Breakpoints of the second highly-supported translocation, t(14,22)(q32.33;q11.22), were located within IGH and IGLL5, which is spanned by the immunoglobulin lambda light chain locus (FIG. 5). Cancer-associated genes within 1 Mb of breakpoint on der(14) are shown in FIG. 5. To validate this translocation, the inventors performed PCR amplification of the putative breakpoint on DNA isolated from the patient in which it was detected. A PCR product of the expected size was detected in CD138+ tumor cells but not in the peripheral blood mononuclear control (FIG. 6 (top)). In FIG. 6: T represents tumor and N represents germline (peripheral blood) control. Re-sequencing and mapping of the tumor-specific PCR product confirmed the reciprocal translocation spanned chromosomes 14 and 22. Small regions were deleted on both derivative chromosomes and thus could be used to selectively amplify the corresponding wild-type chromosomes. The inventors designed primers within these deleted regions and used them to perform PCR amplification, which confirmed the retention of one copy of each of the wild-type chromosomes in the tumor sample (FIG. 6 (bottom)).

Figure 7:
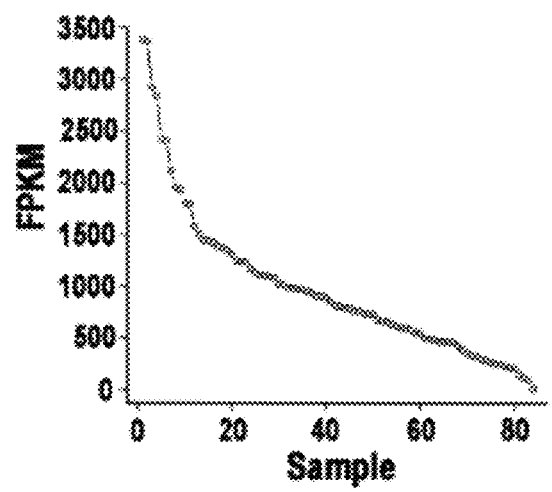
FIG. 7 illustrates DERL3 expression across 84 MM patients.

To search for additional IGLL5 translocations, the inventors relaxed their filtering constraints and found a second sample predicted by LUMPY to harbor a t(14;22) translocation, though no DNA was available for validation. Both 168 t(14;22) translocations were predicted to juxtapose the mu enhancer and/or the 3' enhancer 169 (chr14:106032614-106167601) upstream of DERL3. Hence, the inventors looked for evidence of overexpression of DERL3 and other cancer-associated genes within 1 Mb of the predicted breakpoint on chromosome 22 (IGLL5, BCR, and SMARCB1) by examining RNA-seq expression data from a partially overlapping set of 84 MM patients. Outlying expression of DERL3 was observed in six of these samples (exceeding 1.5× the FPKM interquartile range), including the second sample with a putative t(14;22) translocation (FIG. 7; Red circle indicates sample in which putative (non-validated) t(14;22) translocation was detected; FPKM: Fragments Per Kilobase of transcript per Million mapped reads; no expression data were available for the sample harboring the validated translocation). Additionally, DERL3 was overexpressed in MM relative to other cancer types within the Cancer Cell Line Encyclopedia (Barretina, J. et al., Nature, 2012, 483, 603-607). Taken together, these data illustrate that DERL3 is dysregulated in MM via IGH translocation. Without being limited by theory, proteins misfolded in the endoplasmic reticulum (ER) are degraded by the proteasome in the cytosol via a pathway called ER-associated degradation (ERAD). ERAD is of particular interest in MM because bortezomib, one of the most effective anti-myeloma chemotherapy agents, targets the proteasome. Within this pathway, DERL3 plays a role by forming an export channel in the membrane of the ER through which substrates pass to reach the proteasome that is to be degraded. Malignant cells will have a selective advantage for survival in cases of overexpression of DERL3, and publicly available mRNA expression data has shown higher expression levels of DERL3 in MM. Although this is opposite of the observation that hypermethylation leads to reduced DERL3 expression, which is consistent with a tumor suppressor role, this observation was limited to solid tumors.

Example 6

This example illustrates targeted capture sequencing identifies intra- and inter-chromosomal MYC translocations.

FISH validation data of MYC translocations were not available to tune LUMPY parameters and, as a result, intra- and (non-IGH) inter-chromosomal MYC translocations were called at a high false positive rate (in every tumor and normal sample,). To accurately detect somatic MYC translocations, the inventors developed a machine learning-based approach using a support vector machine (SVM) tuned to filter putative MYC translocations called in normal samples with 100% precision based on number of supporting split and paired-end reads. This allowed the inventors to filter any MYC translocations in tumor samples that were assigned by the SVM to the same class as the normal sample translocations. Applying this method to tumor samples resulted in five intra-chromosomal and two non-IGH inter-chromosomal MYC translocations, with one sample having one intra- and one inter-chromosomal translocation (6 of 95, 6%, FIG. 8; Table 7). The intra-chromosomal translocations involved neighboring genes PVT1 and POU5F1B, as previously reported (Walker, B. A., et al., Blood Cancer J., 2014, 14, 13.) The inventors detected (intra- and inter-chromosomal)

Figure 8:
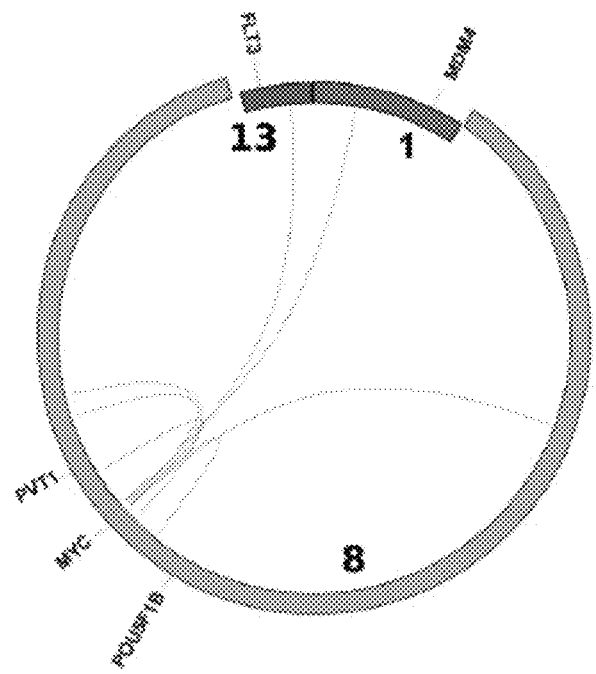
FIG. 8 illustrates a Circos plot of MYC translocations in which chromosomes involved in translocations are magnified to highlight regions and genes near breakpoints.

MYC translocations at a frequency of 13% [95% CI (7%-20%); 12 of 95; FIG. 8; Table 7].

Example 7

This example illustrates targeted capture sequencing identifies non-silent single nucleotide variants in all tumor samples.

All tumor samples harbored at least one somatic (missense, nonsense, or frame shift) mutation, with each sample having a mean of 20 mutations. A total of 443 genes had a non-synonymous (frame-shift insertion or deletion, missense, or nonsense) mutation in one or more samples; 581 genes had a mutation of any kind in one or more samples. Ninety-four of 95 tumor samples had a mutation predicted to be deleterious by Poly-Phen2 (Adzhubei, I. A., et al., Nat. Methods, 2010, 7, 248-249) or SIFT (Kumar, P., Nat. Protoc., 2009, 4, 1073-1081) with each sample having a mean of twelve deleterious mutations. In 24 instances, the inventors observed a gene harboring multiple mutations previously associated with cancer (via COSMIC). This occurred in thirteen samples across seventeen genes including KRAS and RB1; both were among the most frequently observed (in three samples).

Example 8

This example illustrates that increased sequencing depth yields few additional variants.

Figure 9:
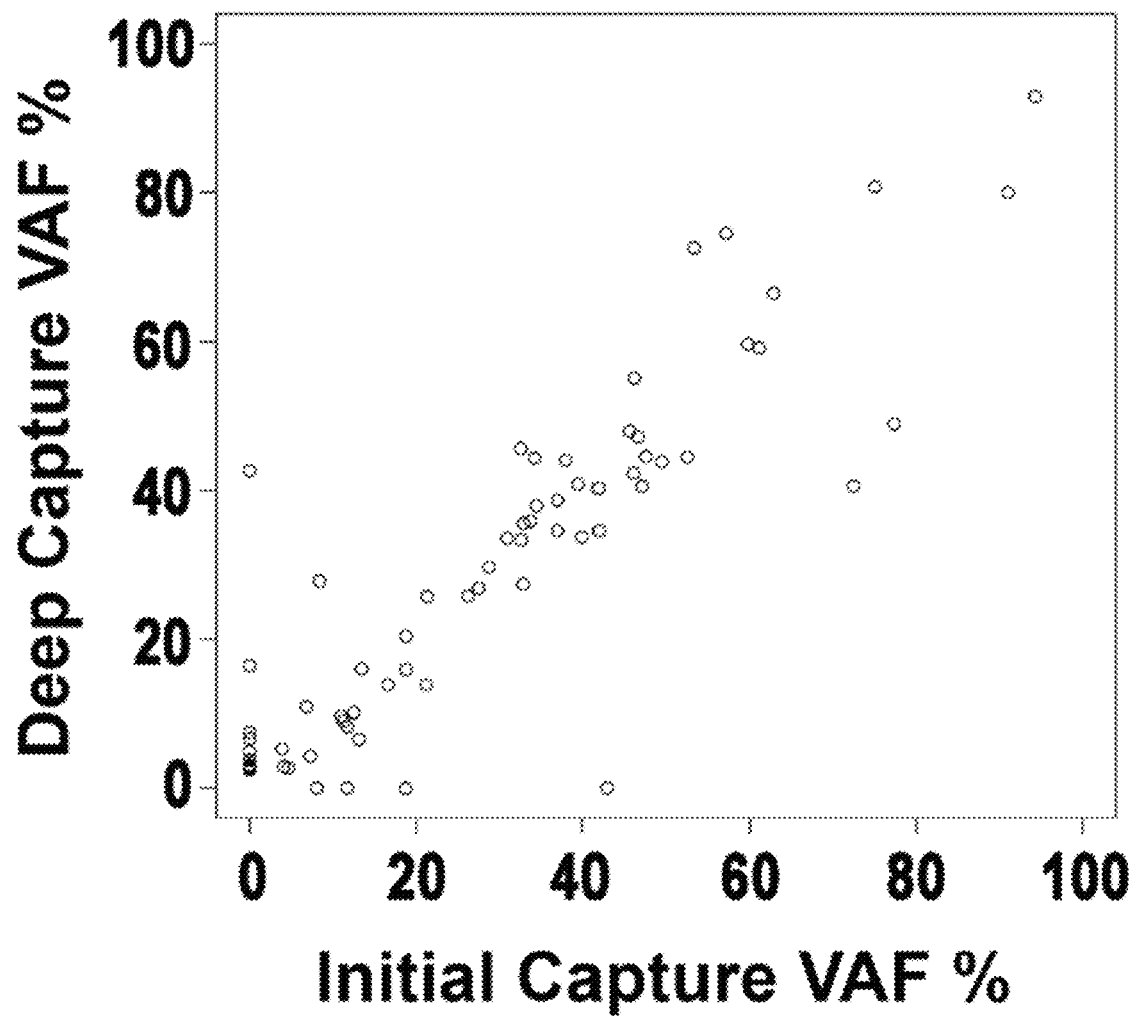
FIG. 9 illustrates variant allele frequency (VAF) of variants discovered during initial targeted sequencing (x axis) and/or with subsequent deeper sequencing (y axis).
Figure 10:
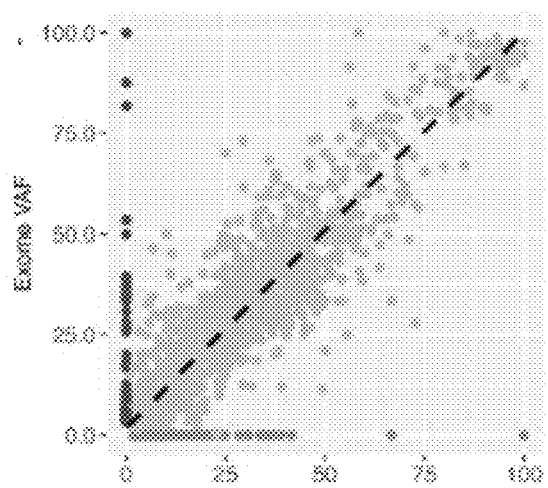
FIG. 10 illustrates VAF of variants discovered by both capture and exome sequencing (gray), by capture sequencing only (green), or by exome sequencing only (blue).
Figure 11:
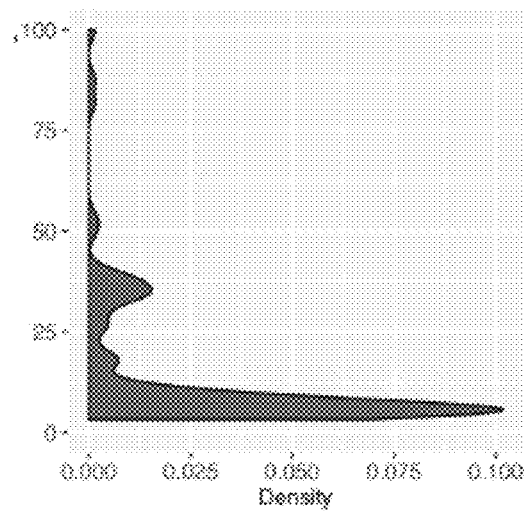
Figure 12:
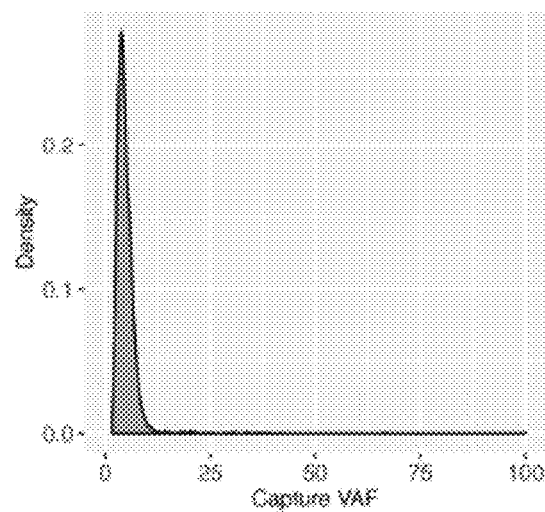
FIG. 12 illustrates VAF (x axis) density (y axis) of capture sequencing-specific variants.

To determine whether MM is characterized by deeply subclonal variants of biological significance, the present inventors performed additional sequencing of 15 tumor (mean depth=1,259×, min=506×, max=1,660×) and paired normal (mean=1,326×, min=763×, max=1,727×) samples. They then compared the allele frequencies of variants discovered during the original and/or subsequent deep sequencing (FIG. 9). To focus on high-confidence events likely to be of biological relevance, the inventors removed silent variants, those in intronic, intergenic, or flanking regions, those in IGH (and, hence, likely arising due to somatic hypermutation), or those that were flagged as likely germline variants by at least one caller in at least one study. This resulted in 57 variants in the original sequencing study (mean depth=92×) and 67 variants in the subsequent study (mean depth=1,169×). Variant allele frequencies (VAFs) within the two studies were highly correlated ($R^2$=0.80; p<2.2e-16). As expected, the vast majority of variants unique to either study had low VAFs: one of the four variants unique to the original study had a VAF<10%, though all had an alternate allele count of three or fewer supporting reads, while 12 of the 14 variants unique to the subsequent study had a VAF<10%. Though relatively few new variants were discovered by the additional sequencing, these did include several annotated in COSMIC in genes KRAS, HECW1, and ZFHX4. These results were recapitulated in a comparison of the variants discovered in 44 samples subjected to capture-based sequencing and previously to exome sequencing (FIG. 10-12). As in the above comparison, the 3,676 variants discovered in one or both studies (mean depth of 1,562 capture-based variants=123×; mean depth of 3,563 exome variants=136×) had highly correlated VAFs ($R^2$=0.85; p<2.2e-16). Again, the majority of variants unique to one study had low VAF: 79 of 112 variants unique to the capture-based study (FIG. 12) and 2,066 of the 2,113 variants unique to the exome-based study (FIG. 11) had VAFs<10%. To further explore the effects of sequencing depth, the inventors downsampled the sequencing reads from the 15 deeply-sequenced samples, called variants on the downsampled reads, and plotted the total number of variants following filtering (as above) in the downsampled and full data set. As expected, the number of variants was correlated with sequencing depth ($R^2$=0.52; p=$10^{-3}$). However, beyond ~25% of the final sequencing depth, the increase in number of discovered variants is marginal.

Example 9

This example illustrates targeted capture sequencing facilitates integrative analysis across mutation types.

Figure 13:
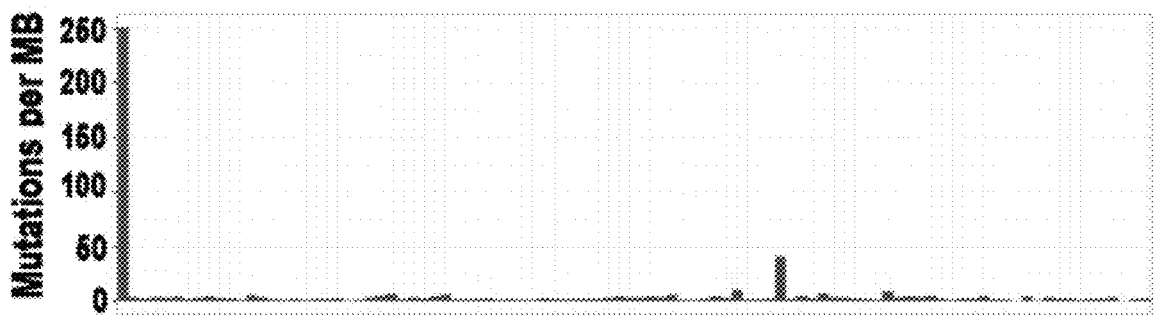
FIG. 13 illustrates mutations per Mb detected across 95 samples (columns) across the various studies.
Figure 14:
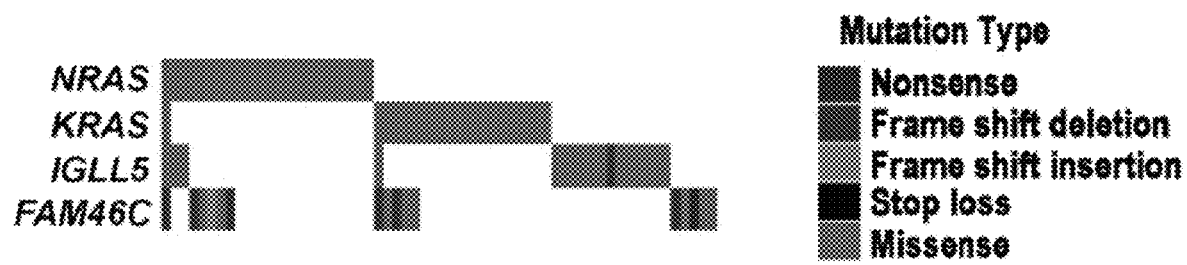
FIG. 14 illustrates SNVs detected across 95 samples (columns) across the various studies.
Figure 15:
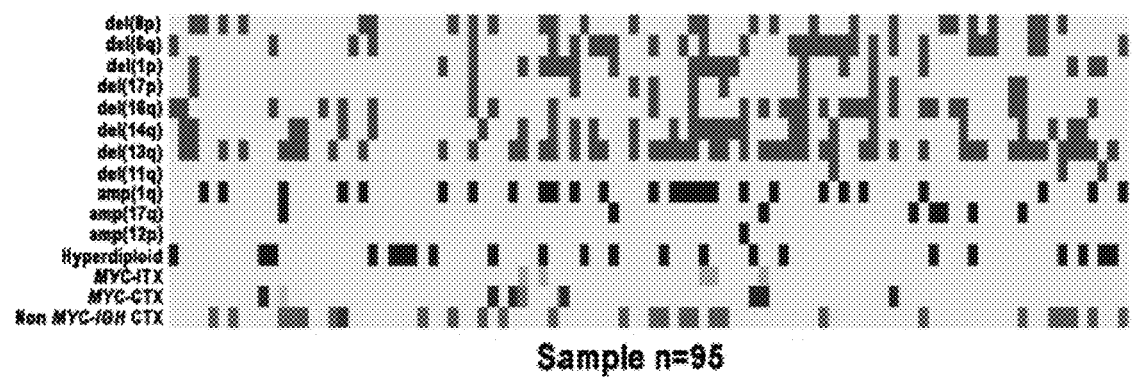
FIG. 15 illustrates CNVs and translocations detected across 95 samples (columns) across the various studies.
Figure 15:
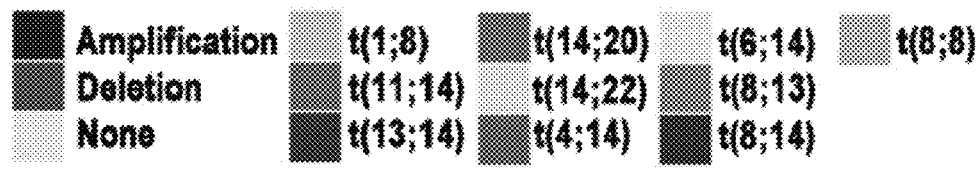
Figure 16:
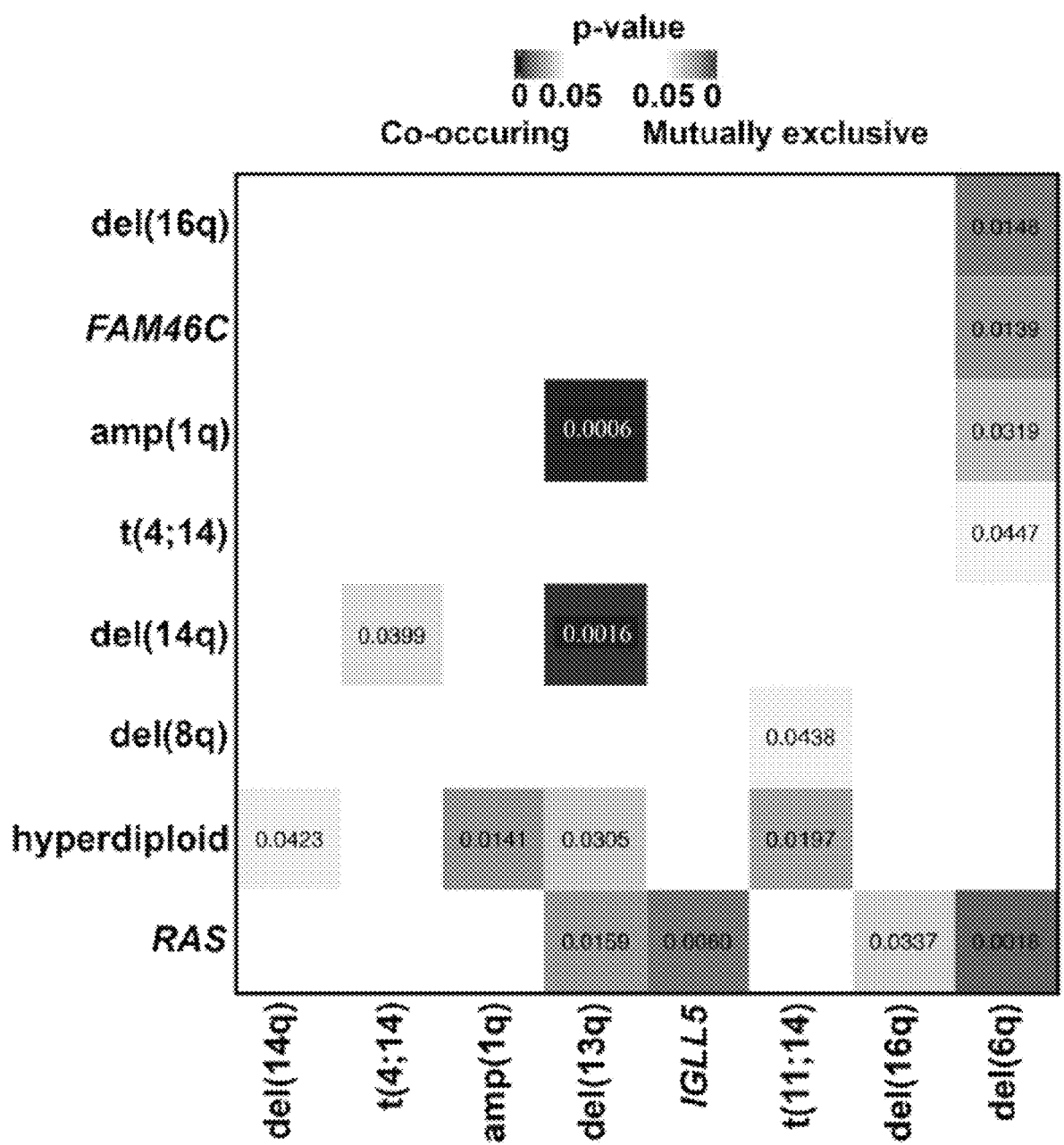
FIG. 16 illustrates identification of co-occurrence and mutual exclusivity across mutation types by targeted sequencing.
Figure 17:
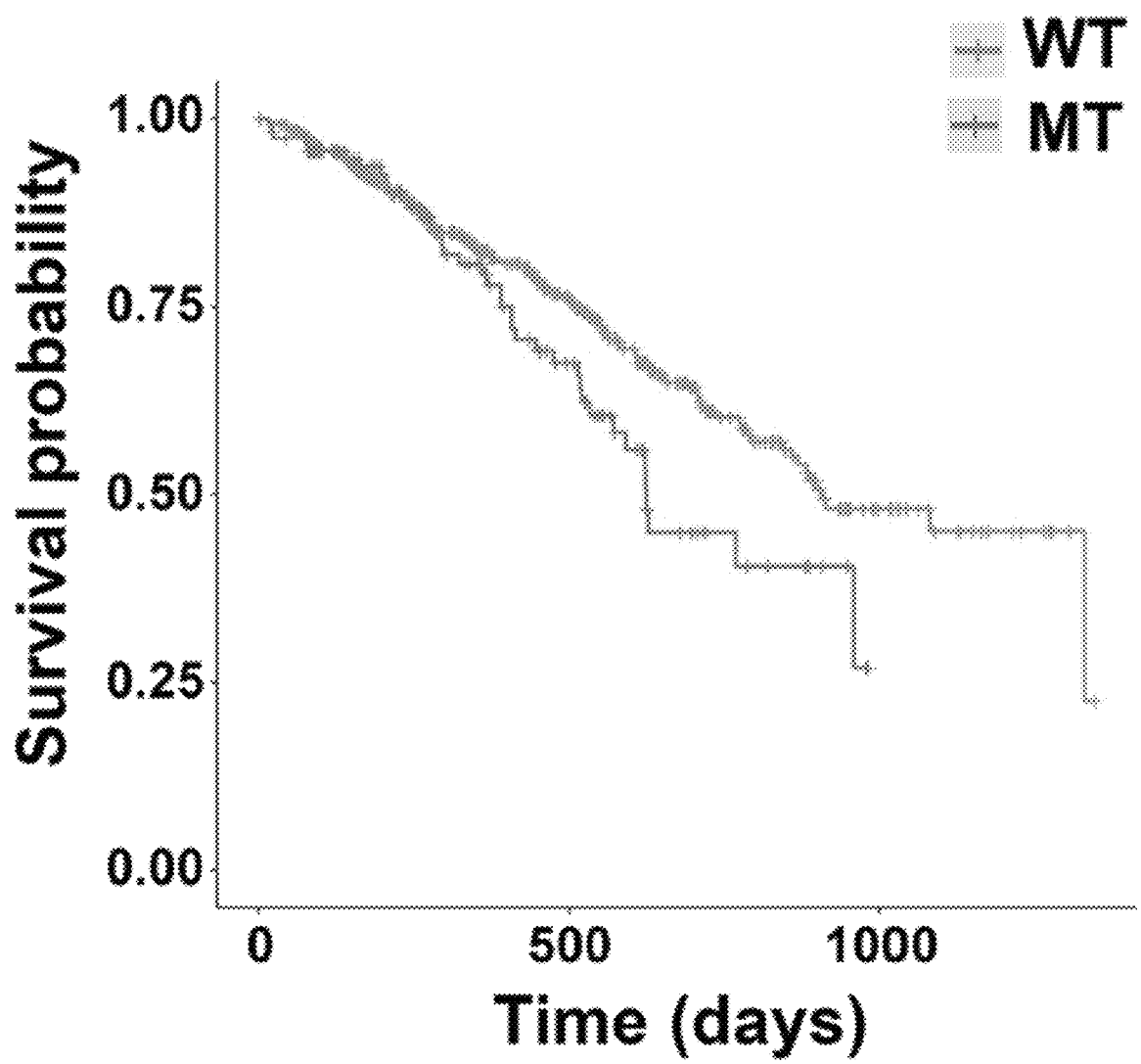
FIG. 17 illustrates that IGLL5 mutations are associated with increased risk of disease progression through Kaplan-Meier curves of IGLL5 mutant samples (with non-synonymous SNVs and/or indels) versus IGLL5 WT samples.

Integrated analysis of CNVs, SNVs, and translocations highlights patterns of mutual exclusivity and co-occurrence both within and across mutation types (FIG. 13-15). For each of FIG. 13-15, MYC-ITX: intra-chromosomal MYC translocations; MYC-CTX: inter-chromosomal MYC translocations; Non MYC-IGH CTX: inter-chromosomal IGH translocations, excluding those involving MYC. The inventors tested for significance of these patterns after excluding the apparent hypermutator sample (leftmost column; FIG. 13) to improve statistical power. This revealed mutation co-occurrence (blue; FIG. 16) within CNVs [i.e., of del(6q) with del(16q) and amp(1q) and of del(13q) with amp(1q) and del(14q)] and involving CNVs and translocations [i.e., of del(14q) with t(4;14)]. As expected, they detected mutual exclusivity (red; FIG. 16) between hyperdiploidy and t(11; 14). In FIG. 16, Co-occurring (blue) and mutually exclusive (red) mutations (p<0.05) are shown. Numbers indicate p-values. The present inventors also detected cross-mutation type exclusivity between CNVs and SNVs [i.e., both RAS mutations (i.e., KRAS or NRAS) and FAM46C are mutually exclusive with del(6q)]. IGLL5 was the third most frequently mutated gene in our data set (FIG. 14; 18%), with (silent and non-synonymous) IGLL5 mutations enriched for a c-AID signature (i.e., C to T/G mutation at WRCY motifs; p=$2.7 \times 10^{-6}$; binomial test). Mutations in IGLL5 were mutually exclusive of RAS mutations (p=0.006), with trends toward mutual exclusivity with KRAS (p=−0.054), NRAS (p=0.111), and FAM46C (p=0.113), independently (FIG. 13-16). IGLL5 mutations in diploid loci had a median VAF of 58% and a first quartile VAF of 39%, suggesting that the majority are likely clonal. Finally, the inventors found that IGLL5 SNVs are associated with disease progression [FIG. 17; hazard ratio=1.46 (95% confidence interval: 1.03-2.08); p=0.03 (log-rank test)].

Example 10

This example illustrates the use of an array of the present teachings to determine the prognosis of a Multiple Myeloma patient.

A patient newly diagnosed with Multiple Myeloma is referred to an Oncologist. In order to determine the patient's long term prognosis, the Oncologist orders genetic testing. Plasma samples comprising B cell tumor cells are collected from the patient. Control samples from the patient's cheek are also collected. A capture array comprising the genes in Table 3 is used to enrich samples, and then these samples are sequenced and compared pairwise between non-tumor/control and tumor cells. The results are obtained within 2 weeks of collecting the samples, and reveal that the patient has a t(4;14) translocation. The Oncologist determines that the patient has a poor's prognosis with a median overall survival of 3.9 years.

Example 11

This example illustrates the use of an array of the present teachings to select treatment of a Multiple Myeloma patient.

An oncologist needs to determine a treatment for a Multiple Myeloma patient and orders genetic testing of the present teachings. Plasma samples comprising B cell tumor cells are collected from the patient. Control samples from the patient's cheek are also collected. A capture array comprising the genes in Table 3 is used to enrich samples, and then these samples are sequenced and the reads between the two tissues are compared pairwise for each gene between non-tumor/controls and tumor cells. The results are obtained within 2 weeks, and reveal that the patient has a BRAF-V600E mutation. The Oncologist, upon seeing these results prescribes low doses of vemurafenib.

Example 12

This example illustrates the use of an array of the present teachings to determine the effectiveness of Multiple Myeloma treatment.

The patient from Example 11 has been undergoing treatment for Multiple Myeloma. The oncologist orders a new round of testing in order to determine the effectiveness of treatment. Plasma samples comprising B cell tumor cells are collected from the patient. Control samples from the patient's cheek are also collected. A capture array comprising the genes in Table 3 is used to enrich samples. These samples are sequenced and the reads between the two tissues are compared pairwise for each gene between healthy and tumor cells. The results show an absence of previously listed abnormalities, t(11;14), t(6;14), and hyperdiploidy, revealing a lack of disease progression.

All publications cited herein are hereby incorporated by reference, each in its entirety.

What is claimed is:

1. A method of identifying multiple myeloma mutations in a subject in need thereof, comprising:
   a) providing a DNA sequencing library comprising genomic DNA obtained from tumor cells of a subject;
   b) providing a DNA sequencing library comprising genomic DNA obtained from non-tumor cells of the subject;
   c) hybridizing the sequencing library comprising the genomic DNA obtained from the tumor to a set of biotinylated oligonucleotide probes, wherein each biotinylated oligonucleotide probe specifically hybridizes to:
   i) a gene of at least 400 genes selected from the following 465 genes: DTNB, DNMT3A, ULK4, TRAK1, DNAH11, CDCA7L, FGFR3, WHSC1, CCND3, CCND1, MAF, MAFB, CKS1B, ANP32E, LTBR, MAP4K4, MYC, CDKN2C, RBI, CDKN2A, NRAS, KRAS, BRAF, PIK3CA, AKT1, TRAF3, CYLD, DKKI, FRZB, DNAH5, XBP1P1, PRDM1, IRF4, TP53, MRE11A, PARP1, DIS3, FAM46C, LRRK2, KDM6A, MLL, HOXA9, KDM6B, FAF1, BIRC2, BIRC3, WWOX, ACTG1, FNDC3A, MAX, TNKS, RPL10, BCL7A, EGR1, SP140, GCET2, HIST1H3G, SNRNP48, BAGE2, MEOX1, FERMT2, PRND, TRIP12, DNAH2, RASA2, PLA2G2D, COBLL1, ATF71P, GSTO2, SLC24A1, AASS, RBM25, ROBO2, THRAP3, ZNF326, GNG7, IF144, STARD13, HAUS3, TTC7B, CDKN1B, RNF151, SLC36A1, FAM153B, ORIL8, PRUNE2, COL4A1, USP50, SAMHD1, CXCR4, CHD2, KRTDAP, PTCH2, FBXO36, ABCC4, UBB, YTHDF2, HUWE1, NLRC5, CDH8, PHOX2B, CDCA2, MOGAT3, PSMD1, EXOG, GRIA2, CCDC144NL, IQSEC1, CKM, SYMPK, DAAM1, PTPRZ1, ORIN2, AGTR2, DUSP28, ADCY8, ACACA, PRIM2, DOLK, CST4, ACSM4, TMCO3, HTR6, OR1S2, NDUFAF3, FAM122C, SLC48A1, HIST1H3H, PNRC1I, NALCN, COL11A2, LCE3A, ZNF431, HERC4, TMEM143, CDC27, FXYD6, OR5P3, MALL, PLXDC2, EGFL6, CELSR2, PHKB, IRX2, PRKD2, STX5, TOM1LI, COX7B2, RNF40, PTPRD, MMP7, YAP1, MSRA, KIAA1377, SOX7, FAM167A, RP1LI, XKR6, CSMD2, PDE4DIP, FLG, HMCN1, RGS2, USH2A, OBSCN, RYR2, ANK3, TACC2, MK167, LRRC4C, FAT3, DYNC2H1, BTG1, EP400, AHNAK2, RYR3, HYDIN, ZFBX3, DNAH9, LAMA1, ZNF208, ZNF257, RYR1, FCGBP, NRXN1, NEB, SCN2A, FRG1B, BSN, ROBO1, KALRN, ANK2, FAT4, TRIO, FAM134B, MYO10, CMYA5, VCAN, FBN2, PKHD1, DST, SYNE1, HECW1, PCLO, PCMTD1, ZFHX4, CSMD3, MLLT3, TRPM3, GJB3, KTI12, DIRAS3, HIST2H3D, HIST2H2BE, HIST2H2AC, HIST3H2A, NAMPTL, RBMXL2, CDC42EP2, KRTAP5-10, FUT4, HIST4H4, ATXN7L3B, PABPC3, SPRY2, GREM1, EID1, IMP3, SOCS1, NACA2, TRAPPC5, RPS28, ZNF493, RPSAP58, FFAR2, EID2B, FAM84A, FOXD4LI, TMEM177, KCNE4, MOV10LI, LRRC3B, RPP14, CGGBP1, H1FX, SLC35G2, CRIPAK, DCAF16, PURA, HIST1H4B, HIST1H2BB, HIST1H3C, HIST1H1C, HIST1H4C, HIST1H2AC, HIST1H1E, HIST1H3E, HIST1H3D, HIST1H2BF, HIST1H4E, HIST1H2AE, HIST1H1D, HIST1H3F, HIST1H4H, HIST1H2BJ, HIST1H2AG, HIST1H2BK, HIST1H2BL, HIST1H2BM, HIST1H2AM, HIST1H2BO, LTB, C2, TBCC, TPBG, CLDN4, PEG10, RNF133, NATI, AQP7, GCNT1, DIRAS2, TMSB4X, CPXCR1, RPA4, TCEAL3, MAGEC3, NOTCH2, EHD1, AKAP6, LRRTM4, VCPIP1, ABCA2, LYPLA2, DTX1, MYOM1, TGFB1, RRBP1, RPRD1B, IGLL5, ZNF148, RNF150, ATM, ARID2, SCAF11, WDR87, SETD2, EXOC4, MAGED1, SLIT3, SLC6A11, ZNF319, ZNF100, ZNF91, ZNF681, ZNF235, ZNF616, ZNF721, KCNH4, GRM7, TJP3, FMN1, TLR5, VDR, ADRA2B, LRRN1, SLIT2, ATR, AICDA, SUPT5H, UNG, CCDC88A, MSH2, NLRP2, PAX5, TCF3, ID2, NFKB1, NFKB2, RELA, PRKACB, PTBP2, APEX1, APEX2, MSH6, TRJM28, SUPT6H, MSH3, MSH5, POLQ, RNF8, RNF168, REV3L, PMS2, PAXIP1, PCNA, MLH1, MLH3, EXO1, XRCC6, XRCC5, LIG4, XRCC4, PRKDC, DCLRE1C, NHEJ1, NBN, RAD50, RBBP8, LIG3, LIG1, XRCC1, BBC3, BCL2L11, PRKCD, BCL2L1, TNFSF13B, RAG1, RAG2, H2AFX, MDC1, TP53BP1, CHEK2, BLM, R1F1, SAMSN1, LILRB3, U2AF1, SF3B1, SRSF2, NADK, DNAJC11, DENND4B, KCNN3, ARHGEF11, CR1, KIF26B, AGAP5, TMEM216, TECTA, ZCRB1, CLIP1, UPF3A, SYNRG, PNKP, 1DH1, RAL-GAPA2, NCOA6, CTCFL, EFCAB6, TOMM70A, INTS12, ANKHD1, ZNF318, PLG, TBP, CNTNAP2, ANKRD18B, PCSK5, SHC3, DDX11, HLA-A, HLA-DRB1, ISPD, ALK, ANTXR2, ARID1A, AXL, BA12, BCORL1, BRCA2, CARD11, CCDC155, CDHR1, CHD3, CNKSR2, DCLK2, DICER1, HOXA4, IFG1R, IKBKB, IL6ST, JAK2, KIT, MED12, MED12L, MERTK, MLL5, MTOR, NBEA, NOTCH1, PIK3C2G, PIM1, PTPN11, PTPN14, ROS1, SKP2, SPOP, ST7, STAT3, TP63, TPTE, XBP1, ZIM3, and ZNF717; or ii) a sequence from a set of sequences tiled in an unbiased fashion from ~50 Kb upstream to ~50 Kb downstream of the IGH locus;

d) sequencing the library comprising the genomic DNA obtained from the tumor cells hybridized to the biotinylated oligonucleotide probes to a maximum average depth of 500×;

e) hybridizing the sequencing library comprising the genomic DNA obtained from the non-tumor cells to the biotinylated oligonucleotide probes;

f) sequencing the library comprising the genomic DNA obtained from the non-tumor cells hybridized to the biotinylated oligonucleotide probes to a maximum average depth of 500×; and g) identifying variants in the genomic DNA obtained from the tumor cells compared to the genomic DNA obtained from the non-tumor cells, thereby identifying individual genetic mutations in multiple myeloma in the subject.

2. A method in accordance with claim 1, wherein the at least 400 genes consist of 465 genes which are altered in multiple myeloma.

3. A method in accordance with claim 1 wherein the biotinylated oligonucleotide probes which are tiled in an unbiased fashion from ~50 Kb upstream to ~50 Kb downstream of the IGH locus include biotinylated oligonucleotide probes within the variable (IGHV), diversity (IGHD), joining (IGHJ), and constant/switch regions.

4. A method in accordance with claim 1, wherein the biotinylated oligonucleotide probes comprise probes that hybridize to NRAS, KRAS, FAM46C, TP53, D1S3, IGLL5 and BRAF.

5. A method in accordance with claim 1, wherein the biotinylated oligonucleotide probes comprise probes that hybridize to ATM, BRCA2, CARD11, CCND1, CCND3, CYLD, DIS3, DNAH5, DNAH11, DNMT3A, FAM46C, FGFR3, JAK2, KDM6A, KDM6B, KIT, KRAS, MAF, MAFB, MTOR, MYC, NFKB1, NOTCH1, NOTCH2, PARP1, RB1, TRAF3, and WHSC1.

6. A method in accordance with claim 1, wherein the biotinylated oligonucleotide probes comprise probes that hybridize to CLIP1, CSMD3, EP400, FMN1, FRG1B, KDM6A, KRAS, LAMA1, MLLT3, MSH2, MSH6, NOTCH1, OR1S2, PAX5, and RB1.

7. A method of identifying multiple myeloma mutations in a subject in need thereof, comprising:

a) providing a DNA sequencing library comprising genomic DNA obtained from tumor cells of a subject;

b) providing a DNA sequencing library comprising genomic DNA obtained from non-tumor cells of the subject;

c) hybridizing the sequencing library comprising the genomic DNA obtained from the tumor to a set of biotinylated oligonucleotide probes, wherein each biotinylated oligonucleotide probe specifically hybridizes to:

i) a gene of at least 400 genes selected from the following 465 genes: DTNB, DNMT3A, ULK4, TRAK1, DNAH11, CDCA7L, FGFR3, WHSC1, CCND3, CCND1, MAF, MAFB, CKS1B, ANP32E, LTBR, MAP4K4, MYC, CDKN2C, RBI, CDKN2A, NRAS, KRAS, BRAF, PIK3CA, AKT1, TRAF3, CYLD, DKKI, FRZB, DNAH5, XBP1P1, PRDM1, IRF4, TP53, MRE11A, PARP1, DIS3, FAM46C, LRRK2, KDM6A, MLL, HOXA9, KDM6B, FAF1, BIRC2, BIRC3, WWOX, ACTG1, FNDC3A, MAX, TNKS, RPL10, BCL7A, EGR1, SP140, GCET2, HIST1H3G, SNRNP48, BAGE2, MEOX1, FERMT2, PRND, TRIP12, DNAH2, RASA2, PLA2G2D, COBLL1, ATF71P, GSTO2, SLC24A1, AASS, RBM25, ROBO2, THRAP3, ZNF326, GNG7, IF144, STARD13, HAUS3, TTC7B, CDKN1B, RNF151, SLC36A1, FAM153B, OR1L8, PRUNE2, COL4A1, USP50, SAMHD1, CXCR4, CHD2, KRTDAP, PTCH2, FBXO36, ABCC4, UBB, YTHDF2, HUWE1, NLRC5, CDH8, PHOX2B, CDCA2, MOGAT3, PSMD1, EXOG, GRIA2, CCDC144NL, IQSEC1, CKM, SYMPK, DAAM1, PTPRZ1, OR1N2, AGTR2, DUSP28, ADCY8, ACACA, PRIM2, DOLK, CST4, ACSM4, TMCO3, HTR6, OR1S2, NDUFAF3, FAM122C, SLC48A1, HIST1H3H, PNRC11, NALCN, COL11A2, LCE3A, ZNF431, HERC4, TMEM143, CDC27, FXYD6, OR5P3, MALL, PLXDC2, EGFL6, CELSR2, PHKB, IRX2, PRKD2, STXS, TOM1L1, COX7B2, RNF40, PTPRD, MMP7, YAP1, MSRA, K1AA1377, SOX7, FAM167A, RP1L1, XKR6, CSMD2, PDE4DIP, FLG, HMCN1, RGS2, USH2A, OBSCN, RYR2, ANK3, TACC2 , MK167, LRRC4C, FAT3, DYNC2H1, BTG1, EP400, AHNAK2, RYR3, HYDIN, ZFBX3, DNAH9, LAMA1, ZNF208, ZNF257, RYR1, FCGBP, NRXN1, NEB, SCN2A, FRG1B, BSN, ROBO1, KALRN, ANK2, FAT4, TRIO, FAM134B, MYO10, CMYA5, VCAN, FBN2, PKHD1, DST, SYNE1, HECW1, PCLO, PCMTD1, ZFHX4, CSMD3, MLLT3, TRPM3, GJB3, KTI12, DIRAS3, HIST2H3D, HIST2H2BE, HIST2H2AC, HIST3H2A, NAMPTL, RBMXL2, CDC42EP2, KRTAP5-10, FUT4, HIST4H4, ATXN7L3B, PABPC3, SPRY2, GREM1, EID1, IMP3, SOCS1, NACA2, TRAPPC5, RPS28, ZNF493, RPSAP58, FFAR2, EID2B, FAM84A, FOXD4L1, TMEM177, KCNE4, MOV10L1, LRRC3B, RPP14, CGGBP1, H1FX, SLC35G2, CRIPAK, DCAF16, PURA, HIST1H4B, HIST1H2BB, HIST1H3C, HIST1H1C, HIST1H4C, HIST1H2AC, HIST1H1E, HIST1H3E, HIST1H3D, HIST1H2BF, HIST1H4E, HIST1H2AE, HIST1H1D, HIST1H3F, HIST1H4H, HIST1H2BJ, HIST1H2AG, HIST1H2BK, HIST1H2BL, HIST1H2BM, HIST1H2AM, HIST1H2BO, LTB, C2, TBCC, TPBG, CLDN4, PEG10, RNF133, NATI, AQP7, GCNT1, DIRAS2, TMSB4X, CPXCR1, RPA4, TCEAL3, MAGEC3, NOTCH2, EHD1, AKAP6, LRRTM4, VCPIP1, ABCA2, LYPLA2, DTX1, MYOM1, TGFB1, RRBP1, RPRD1B, IGLL5, ZNF148, RNF150, ATM, ARID2, SCAF11, WDR87, SETD2, EXOC4, MAGED1, SLIT3, SLC6A11, ZNF319, ZNF100, ZNF91, ZNF681, ZNF235, ZNF616, ZNF721, KCNH4, GRM7, TJP3, FMN1, TLR5, VDR, ADRA2B, LRRN1, SLIT2, ATR, AICDA, SUPT5H, UNG, CCDC88A, MSH2, NLRP2, PAX5, TCF3, ID2, NFKB1, NFKB2, RELA, PRKACB, PTBP2, APEX1, APEX2, MSH6, TRJM28, SUPT6H, MSH3, MSH5, POLQ, RNF8, RNF168, REV3L, PMS2, PAXIP1, PCNA, MLH1, MLH3, EXO1, XRCC6, XRCC5, LIG4, XRCC4, PRKDC, DCLRE1C, NHEJ1, NBN, RAD50, RBBP8, LIG3, LIG1, XRCC1, BBC3, BCL2L11, PRKCD, BCL2L1, TNFSF13B, RAG1, MDC1, TP53BP1, CHEK2, BLM, R1F1, SAMSN1, LILRB3, U2AF1, SF3B1, SRSF2, NADK, DNAJC11, DENND4B, KCNN3, ARHGEF11, CR1, KIF26B, AGAP5, TMEM216, TECTA, ZCRB1, CLIP1, UPF3A, SYNRG, PNKP, 1DH1, RALGAPA2, NCOA6, CTCFL, EFCAB6, TOMM70A, INTS12, ANKHD1, ZNF318, PLG, TBP, CNTNAP2, ANKRD18B, PCSK5, SHC3, DDX11, HLA-A, HLA-DRB1, ISPD, ALK, ANTXR2, ARID1A, AXL, BA12, BCORL1, BRCA2, CARD11, CCDC155, CDHR1, CHD3, CNKSR2, DCLK2, DICER1, HOXA4, IFG1R, IKBKB, IL6ST, JAK2, KIT, MED12, MED12L, MERTK, MLL5, MTOR, NBEA, NOTCH1, PIK3C2G, PTPN11, PTPN14, ROS1, SKP2, SPOP, ST7, STAT3, TP63, TPTE, XBP1, ZIM3, and ZNF717; or ii) a sequence from a set of sequences tiled in an unbiased fashion from ~50 Kb upstream to ~50 Kb downstream of the IGH locus;

d) purifying the library comprising the genomic DNA obtained from the tumor cells hybridized to the biotinylated oligonucleotides, wherein the biotinylated oligonucleotides are immobilized via binding to streptavidin-labeled magnetic beads;

e) sequencing the library comprising the genomic DNA obtained from the tumor cells hybridized to the biotinylated oligonucleotide probes to a maximum average depth of 500×;

f) hybridizing the sequencing library comprising the genomic DNA obtained from the non-tumor cells to the biotinylated oligonucleotide probes;

g) purifying the library comprising the genomic DNA obtained from the non-tumor cells hybridized to the biotinylated oligonucleotides, wherein the biotinylated oligonucleotides are immobilized via binding to streptavidin-labeled magnetic beads;

h) sequencing the library comprising the genomic DNA obtained from the non-tumor cells hybridized to the biotinylated oligonucleotide probes to a maximum average depth of ~500×; and i) identifying variants in the genomic DNA obtained from the tumor cells compared to the genomic DNA obtained from the non-tumor cells, thereby identifying individual genetic mutations in multiple myeloma in the subject.

* * * * *